United States Patent
Yoo et al.

(10) Patent No.: US 6,413,983 B1
(45) Date of Patent: Jul. 2, 2002

(54) BENZOPYRANYL HETEROCYCLE DERIVATIVES, PROCESS FOR PREPARATION THEREOF, AND PHARMACEUTICAL COMPOSITIONS CONTAINING THEM

(75) Inventors: Sung-Eun Yoo, Chungchongnam-do; Sun Kyung Lee, Taejon-si; Kyu Yang Yi, Taejon-si; Nak Jeong Kim, Taejon-si; Jee Hee Suh, Taejon-si; Hwa Sup Shin, Taejon-si; Byung Ho Lee, Taejon-si; Ho Won Seo, Taejon-si; Hong Lim, Seoul; Sun-Ok Kim, Taejon-si; Dongha Lee, Taejon-si; Insun Cho, Taejon-si; Miae Namgung, Taejon-si; Dongsoo Jang, Taejon-si, all of (KR)

(73) Assignee: Dongbu Hannong Chemical Co. Ltd., Seoul (KR)

( * ) Notice: Subject to any disclaimer, the term of this patent is extended or adjusted under 35 U.S.C. 154(b) by 0 days.

(21) Appl. No.: 09/724,029

(22) Filed: Nov. 28, 2000

(30) Foreign Application Priority Data

Oct. 9, 2000 (KR) .......................................... 2000-59354

(51) Int. Cl.⁷ .......................... A01N 43/42; A01K 31/47
(52) U.S. Cl. ...................................................... 514/314
(58) Field of Search ................................ 546/153, 167; 514/314, 414; 548/463, 454

(56) References Cited

U.S. PATENT DOCUMENTS 5,310,932 A * 5/1994 Atwal
5,719,155 A * 2/1998 Cho

OTHER PUBLICATIONS

Treatment of Myocardial Ischemia with ATP–Sensitive Potassium Channel (KATP) Openers, By Atwal et al., Current Pharmaceutical Design, 1996, vol. 2, pp. 585–595.

Cardioselective Anti–Ischemic ATP–Sensitive Potassium Channel Openers. 3. Structure . . ., By Atwal et al., J. Med. Chem. 1995, vol. 38, pp. 3236–3245.

Cardioselective Antiischemic ATP–Sensitive Potassium Channel (KATP) Openers. 6. Effect . . ., By Ding et al., J. Med. Chem. 1999, vol. 42, pp. 3711–3717.

Pharmacology of ATP–Sensitive Potassium Channel (KATP) Openers in Models of Myocardial Ischemia and Reperfusion, By Gary J. Grover, Can. J. Physiol, Pharmacol, vol. 75, pp. 309–315, 1997.

* cited by examiner

Primary Examiner—D. Margaret Seaman
(74) Attorney, Agent, or Firm—Bachman & LaPointe, P.C.

(57) ABSTRACT

The present invention relates to novel benzopyranyl heterocycle derivatives of the formula 1, process for preparation thereof and pharmaceutical use of the benzopyranyl heterocycle derivatives. The benzopyranyl heterocycle derivatives of the present invention can be used for protecting heart, brain, retina and neuronal cell from "ischemia-reperfusion" injury, treatment for diseases related to it and suppressing lipid peroxidation.

FORMULA 1

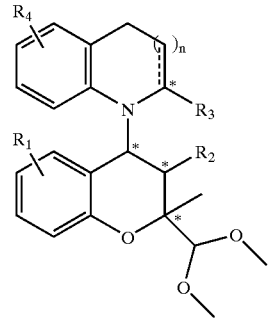

Wherein $R_1$, $R_2$, $R_3$, $R_4$, n and * are each defined in specification.

17 Claims, No Drawings

BENZOPYRANYL HETEROCYCLE DERIVATIVES, PROCESS FOR PREPARATION THEREOF, AND PHARMACEUTICAL COMPOSITIONS CONTAINING THEM

BACKGROUND OF THE INVENTION

1. Field of the Invention

The present invention relates to novel benzopyranyl heterocycle derivatives of the structural formula 1. It also relates to process for preparing the novel compounds and pharmaceutical compositions comprising the compounds as an active ingredient.

The present invention also relates to pharmaceutical use of the benzopyranyl heterocycle derivatives. In particular, the present invention is useful in the prevention, treatment of diseases related to "ischemia-reperfusion" injury such as ischemic heart, brain, neuronal cells and retina, and suppression of lipid peroxidation.

FORMULA 1

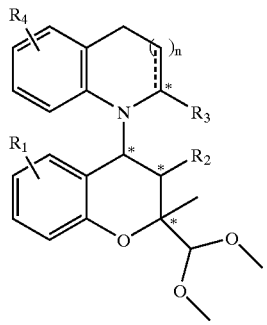

Wherein $R_1$, $R_2$, $R_3$, $R_4$, n and * are each defined in specification.

2. Description of the Prior Art

Ischemic heart diseases are usually caused by myocardial ischemia, when the oxygen supply is significantly decreased compared to the oxygen demand due to the imbalance between them [G. J. Grover, *Can. J. Physiol.* 75, 309 (1997); G. D. Lopaschuk et al. *Science & Medicine* 42 (1997)]. Myocardial ischemia triggers various pathophysiological changes progressively that will ultimately lead to irreversible myocardial injury, cell death and tissue necrosis. At a stage where the injury to the cells is reversible, this process can be prevented by early reperfusion of the myocardium. However, there is potential for "reperfusion-injury" to occur [D. J. Hearse, *Medicographia* 18, 22 (1996)].

To delay the ischemic cascade and to minimize the reperfusion-injury, the use of adenosine agonists, inhibitors of $Na^-$—$K^-$ antiport, oxygen free radical scavengers and $K_{ATP}$ (ATP sensitive potassium channel) openers are investigated as well as ACE (Angiotensin converting enzyme) inhibitors and calcium antagonists. In addition, global ischemia occurs during cardiac surgery or during heart storage prior to transplantation. Recent studies reported that the addition of $K_{ATP}$ openers to a hyperkalemic cardioplegic solution, improved the recovery of postischemic contractile function after normothermic or short periods of hypothermic ischemia [D. J. Chambers, D. J. Hearse, *Ann. Thoar. Surg.*; 68, 1960 (1999)].

Both global and focal ischemia or hypoxia initiate progressive cellular changes by a reduction of oxygen, which lead to brain injury, cell death, and tissue necrosis [K. Nieber, *Pharmacol. Ther.* 82, 71 (1999)]. Even after blood flow is restored, "reperfusion-injury" can be occurred same as in the heart. In order to prevent the brain injury and minimize the alteration of neuronal function, progressive pathophysiological changes arose from ischemia-reperfusion must be prevented. For that purpose, the development of several neuroprotectives such as excitatory amino acid antagonists, anti-oxidants, adenosine agonists and $K_{ATP}$ channel openers are being pursued. The use of those compounds as protectants or curatives for the organs related to "ischemia-reperfusion injury" such as retina and skeletal muscles besides heart and brain, is being investigated, too.

Damage or death of neuronal cells is known to be a main reason for various neurological disorders such as stroke, Alzheimer's disease, Parkinson's disease, etc. [G. J. Zoppo et al., *Drugs* 54, 9(1997); I. Sziraki et al., *Neurosci.* 85, 1101 (1998)]. Various factors including increases in iron concentration, reactive oxygen species, and oxidants within neurons are known to initiate neuronal cell damages [M. P. Mattson et al., *Methods Cell Biol.* 46, 187 (1995); Y. Goodman et al., *Brain Res.* 706, 328 (1996)].

An increase of oxygen radicals may induce a lipid peroxidation, and thus their formation results in the accumulation of oxidants in neuronal cell. The oxidants accumulated in cells are known to be responsible for cardiac infarction, dementia, and inflammatory diseases such as arthritis as well as acute and chronic injury of tissues and organs caused by ischemia-reperfusion.

Therefore, therapeutic approaches to minimize neuronal injury by oxidative stress and inhibit lipid peroxidation have been pursued, which may prevent or treat the deseases caused by the damage or death of neuronal cells. To date, anti-oxidants are reported to ameliorate the neuronal damage and death caused by an increase of iron concentration within neurons. Much effort has been continued to develop pharmaceutical drugs which are able to prevent neuronal damage by oxidative stress [Y. Zhang et al., *J. Cereb. Blood Flow Metab.* 13, 378 (1993)]. Diazoxide, a $K_{ATP}$ channel opener, has been reported to reversibly oxidize flavoproteins in mitochondria, resulting in inhibition of the formation of oxygen free radicals, which may protect cell injury by oxidative stress [A. A. Starkov, *Biosci, Rep.* 17, 273 (1997); V. P. Skulachev, *Q. Rev. Biophus.* 29, 169 (1996)]. In addition, there are reports that $K_{ATP}$ opening is related to the induction of anti-oxidant enzymes [S. Okubo et al., *Mol. and cell Biochem,* 196, 3 (1999)], and to decrease the release of excitatory amino acid [J-L Moreau, G. Huber, *Brain Res.,* 31, 65 (1999)].

$K_{ATP}$ is found in a variety of tissues including cardiac muscle, skeletal muscle, pancreatic (β-cells, and the brain, which makes it attractive as a drug target. However, the same diversity poses a difficulty of finding tissue selective agents. Differently from conventional potassium channel openers, the benzopyranyl indole analogue represented by the following formula 2 and benzopyranyl cyanoguanidine compound (BMS-180448) represented by the following formula 3, have been reported to show modest antiischemic potency with excellent cardiac selectivity. Although the compound represented by formula 2 had all desirable features to serve as a lead compound, the synthesis of it presented a major challenge [K. S. Atwal et al., *J. Med. Chem.* 38, 3236 (1995); K. S. Atwal et al.,*J. Med. Chem.* 40, 24 (1996); K. S. Atwal et al., *Current Pharmaceutical Design,* 2, 585 (1996)]. Also, the conventional compounds, which have cardioprotective potency without a significant lowering of blood pressure, still give the prospects for the development of a novel cardioprotectant.

FORMULA 2

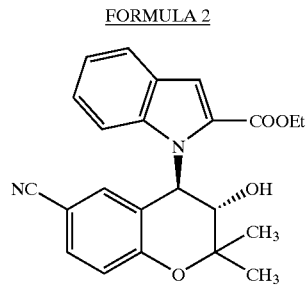

FORMULA 3

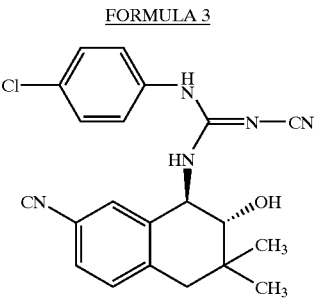

FORMULA 1

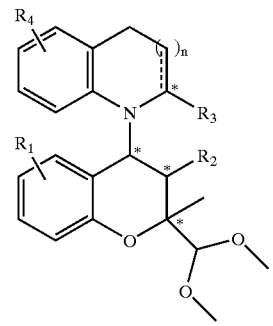

Wherein
n is 0 or 1;
$R_1$ represents H, $NO_2$, or $NH_2$;
$R_2$ represents OH, or $O(C=O)R^a$; and $R^a$ represents H; straight or branched alkyl group of $C_1-C_4$; or aryl group;
$R_3$ represents H, $C(=O)OR^a$, $CH_2OR^a$, or $C(=O)NR^a{}_2$; and $R^a$ is defined as above;
or $R_2$ and $R_3$ are connected to form lactone ring

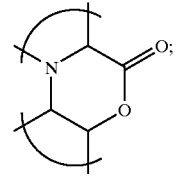

$R_4$ represents H, halogen, OH, or $OR^a$; and $R^a$ is defined as above;
* represents the chiral center;
and single or double bond exists at 2,3-position of heterocycle.
In the formula 1, more preferably
n is 0 or 1;
$R_1$ represents $NO_2$ or $NH_2$;
$R_2$ represents OH;
$R_3$ represents $C(=O)OR^a$, or $C(=O)NR^a{}_2$; and $R^a$ represents H; or straight or branched alkyl group of $C_1-C_4$;
or $R_2$ and $R_3$ are connected to form lactone ring

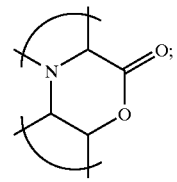

$R_4$ represents H, halogen, OH, or $OCH_3$.
* represents the chiral center;
and single or double bond exists at 2,3-position of heterocycle.
The present invention includes all the solvates and hydrates which can be prepared from benzopyranyl heterocycle derivatives of formula 1 in addition to benzopyranyl heterocycle derivatives of formula 1 and their pharmaceutically acceptable salts.

Therefore, by the coupling of benzopyranyl epoxide and heterocyclic amine compounds which have increased nucleophilicity compared to indoleamines, the benzopyranyl heterocycle derivatives represented by the formula 1, having superior cardioprotective activity from ischemia-reperfusion damage, are synthesized in high yields. The compounds also exhibit various pharmaceutical efficacies, including protection of neuronal cells and prevention of lipid peroxidation and thus can be useful in the prevention and treatment of various diseases related to ischemia-reperfusion damage such as protection of heart, neuronal cells, retina, brain injury, and organ preservation for storage, or inhibition of lipid peroxidation.

SUMMARY OF THE INVENTION

One of the objectives of the present invention is to provide novel benzopyranyl heterocycle derivatives of formula 1.

Another objective of the present invention is to provide process for the preparation of the benzopyranyl heterocycle derivatives.

Further objective of the present invention is to provide pharmaceutical use of the benzopyranyl heterocycle derivatives. In particular, the present invention provides the use of the benzopyranyl heterocycle derivatives for the protection of heart, brain, retina from ischemic injury or protection of organ for storage, and suppression of lipid peroxidation.

DETAILED DESCRIPTION OF THE INVENTION

The present invention provides benzopyranyl heterocycle derivatives represented by the following formula 1 and their pharmaceutically acceptable salts.

The present invention includes all the separate stereochemical isomers, i.e. diastereomerically pure or enantiomerically pure compounds which have one or more chiral centers at 2, 3, 4 and 2'-positions, in addition to the racemic mixtures or diastereomer mixtures of benzopyranyl heterocycle derivatives of formula 1. In case of having four chiral centers at 2, 3, 4 and 2'-positions, the 3,4-dihydro benzopyran heterocycle derivatives according to the present invention are represented by the optical isomers such as ($I_1$), ($I_2$), ($I_3$), ($I_4$), ($I_5$) ($I_6$), ($I_7$) and ($I_8$) (See the following formula 4).

Formula 4

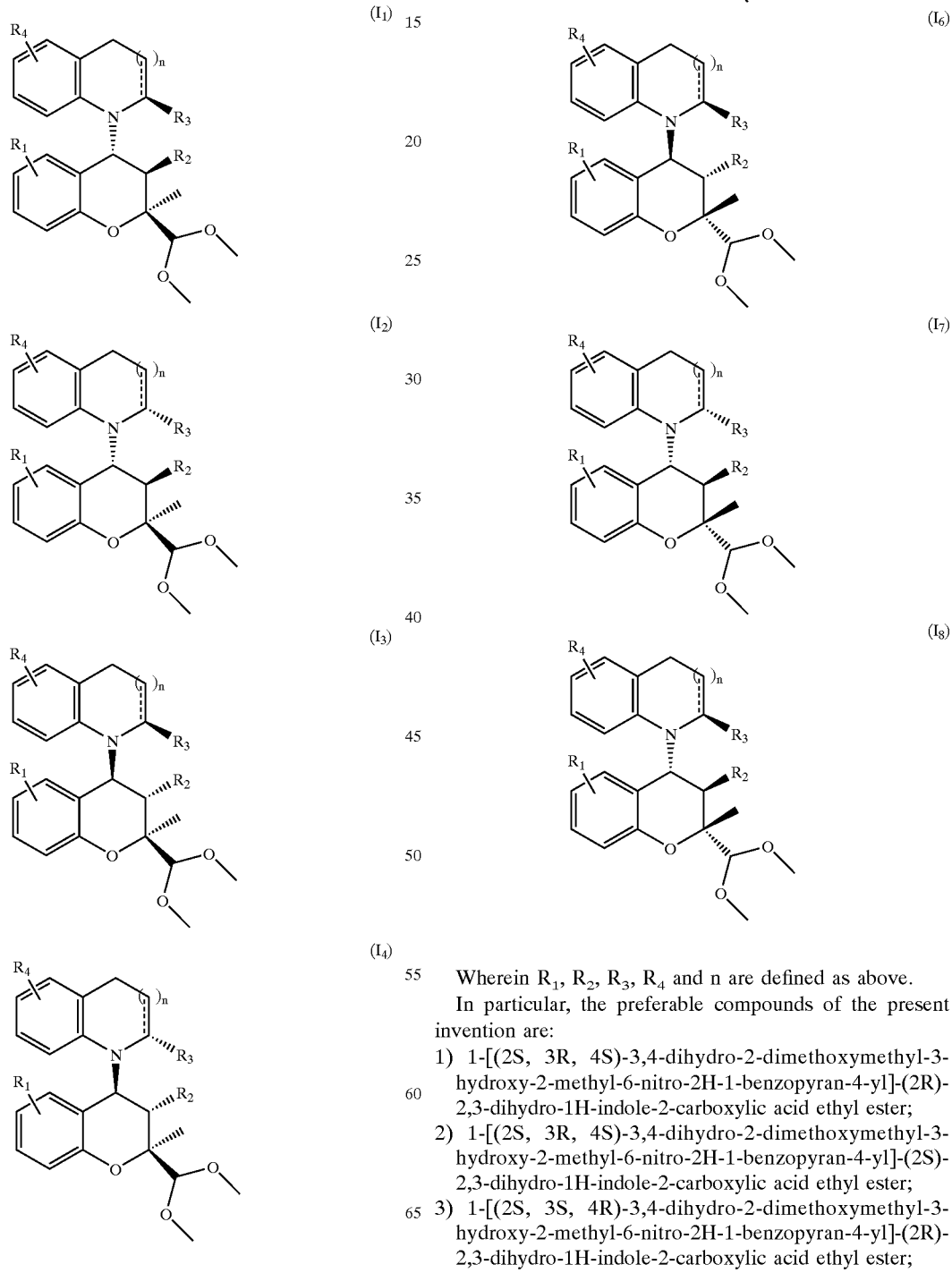

Wherein $R_1$, $R_2$, $R_3$, $R_4$ and n are defined as above.

In particular, the preferable compounds of the present invention are:

1) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;

2) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;

3) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;

4) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
5) 1-[(2S, 3R, 4S)-3,4-dihydro-2-dimethoxymethyl-3-hydroxy-2-methyl-6-nitro-2H-1-benzopyran-4-yl]-1H-(2R)-2,3-dihydroindole-2-carboxylic acid methyl ester;
6) 1-[(2S, 3R, 4S)-3,4-dihydro-2-dimethoxymethyl-3-hydroxy-2-methyl-6-nitro-2 H-1-benzopyran-4-yl]-1H-(2S)-2,3-dihydroindole-2-carboxylic acid methyl ester;
7) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid methyl ester;
8) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid methyl ester;
9) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid;
10) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid isopropyl ester;
11) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
12) 1-[(2S, 3R, 4S)-3,4-dihydro-2-dimethoxymethyl-3-hydroxy-2-methyl-6-nitro-2 H-1-benzopyran-4-yl]-(2S)-2,3-dihydro-1H-5-methoxyindole-2-carboxylic acid ethyl ester;
13) 1-[(2S, 3S, 4R)-3,4-dihydro-2-dimethixymethyl-3-hydroxy-2-methyl-6-nitro-2H-1-benzopyran-4-yl]-(2R)-2,3-dihydro-1H-5-methoxyindole-2-carboxylic acid ethyl ester;
14) 1-[(2S, 3S, 4R)-3,4-dihydro-2-dimethoxymethyl-3-hydroxy-2-methyl-6-nitro-2H-1-bezopyran-4-yl]-(2S)-2,3-dihydro-1H-5-methoxyindole-2-carboxylic acid ethyl ester;
15) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-fluoroindole-2-carboxylic acid ethyl ester;
16) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-fluoroindole-2-carboxylic acid ethyl ester;
17) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-fluoroindole-2-carboxylic acid ethyl ester;
18) 1-[(2S, 3S, 4R)-3,4-dihydro-2-dimethoxymethyl-3-hydroxy-2-methyl-6-nitro-2 H-1-benzopyran-4-yl]-(2S)-2,3-dihydro-1H-5-fluoroindole-2-carboxylic acid ethyl ester;
19) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester;
20) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
21) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester;
22) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
23) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid methyl ester;
24) 1-[(2S, 3S, 4R)-3,4-dihydro-2-dimethoxymethyl-3-hydroxy-2-methyl-6-nitro-2 H-1-benzopyran-4-yl]-(2S)-2,3-dihydro-1H-5-chloroindole-2-carboxylic acid methyl ester;
25) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl amide;
26) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl amide;
27) 1[-(2S, 3R, 4S)-3,4-dihydro-2-dimethoxymethyl-3-hydroxy-2-methyl-6-nitro-2H-1-benzopyran-4-yl]-(2R)-2,3-dihydro-5-chloro-1H-2-hydroxymethylindole;
28) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-5-chloro-1H-2-hydroxymethylindole;
29) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
30) 1-[(2R, 3S, 4R)-3,4-dihydro-2-dimethoxymethyl-3-hydroxy-2-methyl-6-nitro-2 H-1-benzopyran-4-yl]-(2R)-2,3-dihydro-1H-indole-2-carboxylic acid ethyl ester;
31) 1-[(2R, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
32) 1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
33) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid n-propyl ester;
34) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid n-propyl ester;
35) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
36) 1-[(2R, 3S, 4R)-3,4-dihydro-2-dimethoxymethyl-3-hydroxy-2-methyl-6-nitro-2 H-1-benzopyran-4-yl]-(2R)-2,3-dihydro-1H-5-methoxyindole-2-carboxylic acid ethyl ester;
37) 1-[(2R, 3R, 4S)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
38) 1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
39) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl amide;

40) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;

41) 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester;

42) 1-[(2S, 3R, 4S)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester;

43) 1-[(2S, 3R, 4S)-6-amino-3,4-dihydro-2-dimethoxymethyl-3-hydroxy-2-methyl-2H-1-benzopyran-4-yl]-(2S)-2,3-dihydro-1H-indole-2-carboxylic acid ethyl ester;

44) 1-[(2S, 3S, 4R)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester;

45) 1-[(2S, 3S, 4R)-6-amino-3,4-dihydro-2-dimethoxymethyl-3-hydroxy-2-methyl-2H-1-benzopyran-4-yl]-(2S)-2,3-dihydro-1H-indole-2-carboxylic acid ethyl ester;

46) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid ethyl ester;

47) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid ethyl ester;

48) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid methyl ester;

49) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid methyl ester;

50) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid;

51) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid;

52) 1-[(2S, 3R, 4S)-6-amino-3,4-dihydro-2-dimethoxymethyl-3-hydroxy-2-methyl-2H-1-benzopyran-4-yl]-1H-indole-2-carboxylic acid ethyl ester;

53) 1-[(2S, 3S, 4R)-6-amino-3,4-dihydro-2-dimethoxymethyl-3-hydroxy-2-methyl-2H-1-benzopyran-4-yl]-1H-indole-2-carboxylic acid ethyl ester;

54) 1-[(2S, 3R, 4S)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester;

55) 1-[(2S, 3S, 4R)-3,4-dihydro-2-dimethoxymethyl-3-hydroxy-2-methyl-6-nitro-2H-1-benzopyran-4-yl]-(2S)-1,2,3,4-tetrahydro-1H-quinoline-2-carboxylic acid methyl ester;

56) 1-[(2S, 3S, 4R)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester;

57) 1-[(2S, 3S, 4R)-3,4-dihydro-2-dimethoxymethyl-3-hydroxy-2-methyl-6-nitro-2H-1-benzopyran-4-yl]-(2S)-1,2,3,4-tetrahydro-1H-quinoline-2-carboxylic acid methyl ester;

58) (2S, 2aR, 4aR, 10aS)-[(3,4-b)-2a,10a-dihydro-2-dimethoxymehyl-2-methyl-12-nitro-2H-1-benzopyrano]-[(1,2-d)-4a,5-dihydro-10H-indolino]-4-oxomorpholine;

59) (2S, 2aR, 4aS, 10aS)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;

60) (2S, 2aS, 4aR, 10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;

61) (2S, 2aS, 4aS, 10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;

62) (2S, 2aR, 10aS)-[(3,4-b)-2a,10a-dihydro-2-dimethoxymethyl-2-methyl-12-nitro-2H-1-benzopyrano]-[(1,2-d)-10H-indolino]-4-oxomorpholine; or 63) (2S, 2aS, 10aR)-[(3,4-b)-2a,10a-dihydro-2-dimethoxymethyl-2-methyl-12-nitro-2H-1-benzopyrano]-[(1,2-d)-10H-indolino]-4-oxomorpholine.

The more preferable compounds of the present invention are:

1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;

1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;

1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;

1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;

1-[2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;

1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;

1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester; and 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester.

The compounds of formula 1 may be used as pharmaceutically acceptable salts derived from pharmaceutically or physiologically acceptable free acids. These salts include but are not limited to the following: salts with inorganic acids such as hydrochloric acid, hydrobromic acid, sulfuric acid, sulfonic acid, phosphoric acid, stannic acid, etc. and organic acids such as citric acid, acetic acid, lactic acid, maleic acid, fumaric acid, gluconic acid, methanesulfonic acid, glycolic acid, succinic acid, tartaric acid, 4-toluenesulfonic acid, galacturonic acid, embonic acid, glutamic acid, aspartic acid, etc. The acid salts of the compounds according to the present invention can be prepared in the customary manner, for example by dissolving the compound of formula 1 in excess aqueous acid and precipitating the salt with a water-miscible organic solvent, such as methanol, ethanol, acetone or acetonitrile. It is also possible to prepare by heating equivalent amounts of the compound of formula 1 and an acid in water or an alcohol, such as glycol monomethyl ether, and then evaporating the mixture to dryness or filtering off the precipitated salt with suction.

Also the compounds of formula 1 may be in the form of pharmaceutically acceptable ammonium, alkali metals or alkaline earth metals salts. The alkali metal or alkaline earth metal salts of the compound of formula 1 can be obtained, for example, by dissolving the compound of formula 1 in exess alkali metal or alkaline earth metal hydroxide solution, filtering off the undissolved materials and evaporating the filtrate to dryness. Sodium, potassium or calcium salts are pharmaceutically suitable. The corresponding silver salts are obtained by the reaction of an alkali metal or alkaline earth metal salt with a suitable silver salt, such as silver nitrate.

In addition, the present invention provides processes for preparing of the benzopyranyl heterocycle derivatives of formula 1.

In particular, the present invention provides processes for preparing the benzopyranyl heterocycle derivatives of formula 1, represented by the following scheme 1.

SCHEME 1

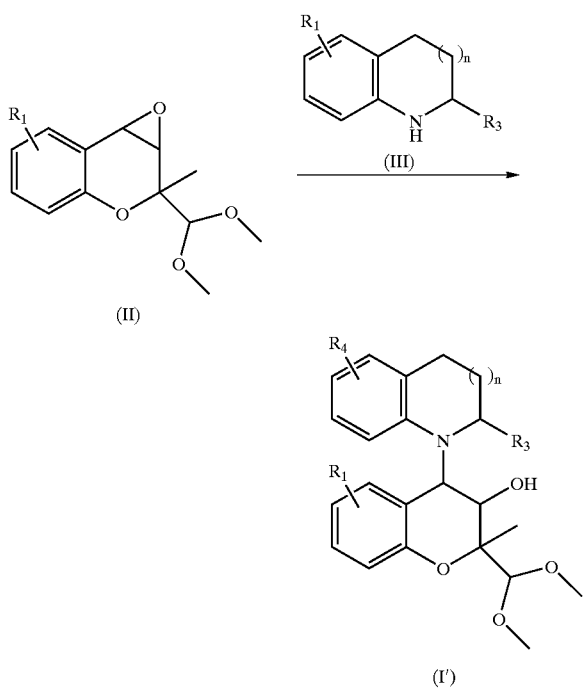

Wherein $R_1$, $R_3$, $R_4$ and n are each defined as above.

In addition, the present invention provides processes for preparing the benzopyranyl heterocycle derivatives of formula 1 by using the compound (I') prepared in the scheme 1, represented by the following scheme 2.

SCHEME 2

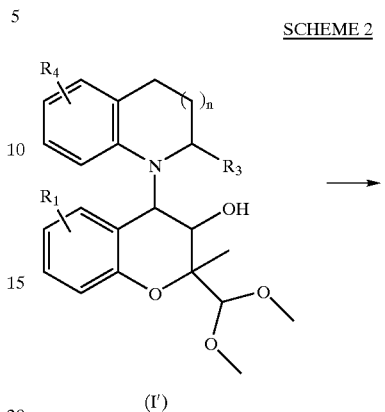

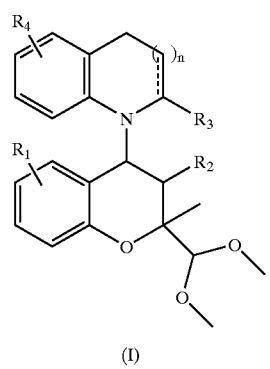

Wherein $R_1$, $R_2$, $R_3$, $R_4$ and n are each defined as above.

The substituents of $R_1$, $R_2$, $R_3$ and $R_4$ can be modified or 2,3-double bond in heterocycle can be formed via the reaction represented by the above scheme 2.

The derivatives of formula 1 can be prepared separately as an optically active isomer by using the corresponding optical isomer as a starting material.

In case of using a racemic mixture as a starting material, the derivatives of formula 1 are prepared as a racemic or a diastereomeric mixture, which can be separated into each optical isomers. The optical isomers can be separated by common chiral column chromatography or recrystallization.

The compounds of formula 1 can be synthesized using the reactions and techniques described herein below. The reactions are performed in a solvent appropriate to the reagents and materials employed and suitable for the transformation being effected.

I. Preparation of Starting Materials

Epoxy compounds (II) which were used as a starting material in scheme 1, can be prepared by the reaction represented by the following scheme 3.

SCHEME 3

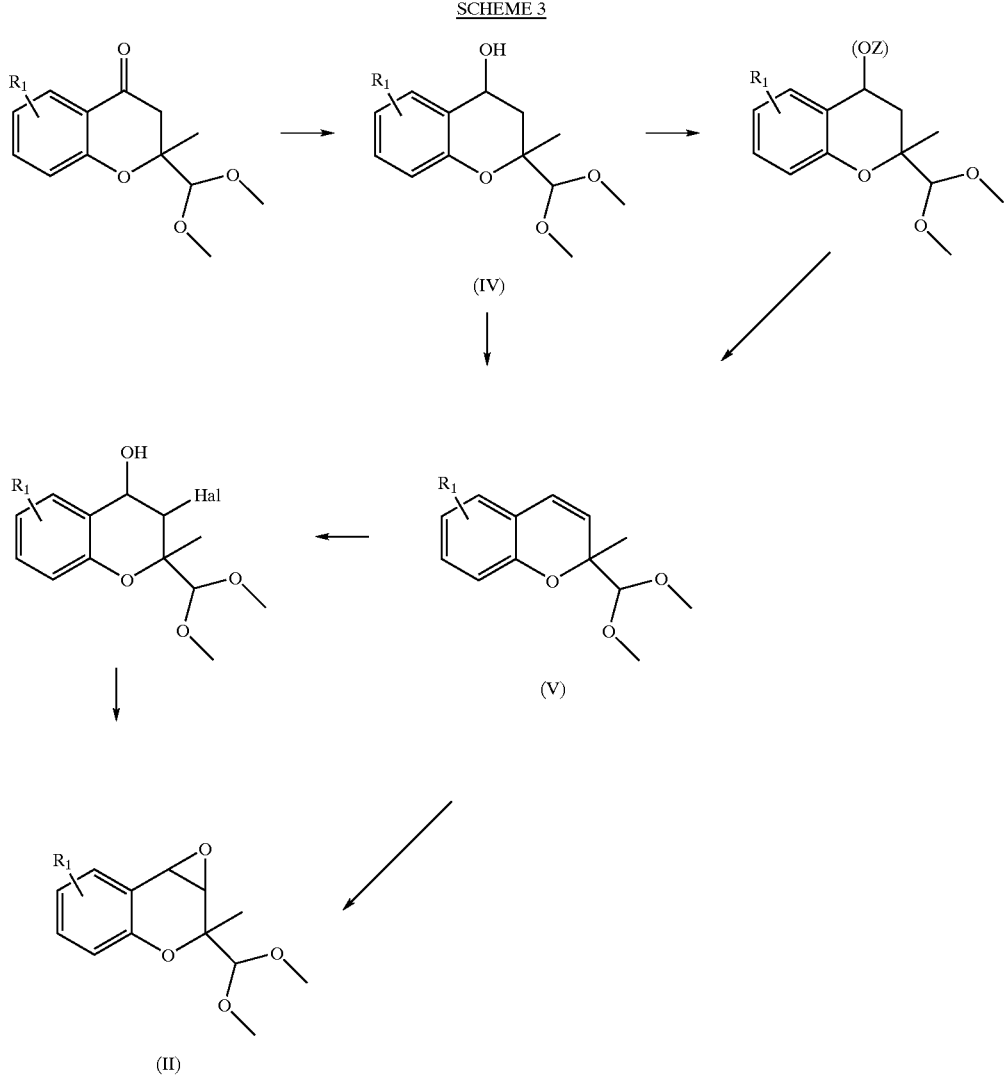

Wherein $R_1$ is defined as above, (OZ) represents a leaving group and Hal represents a halogen atom.

The method for the preparation of the epoxide compound (II) represented by the above scheme 3 is described in U.S. Pat. No. 5,236,935 and KR Pat. No. 096,546 which were acquired by the present inventors, in detail.

(1) Preparation of Olefin Compounds (V)

Olefin compounds (V) exist as enantiomers ($V_1$ and $V_2$) such as formula 5.

FORMULA 5

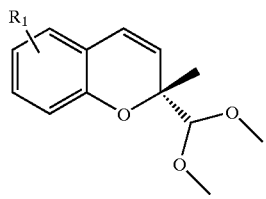

($V_1$)

-continued

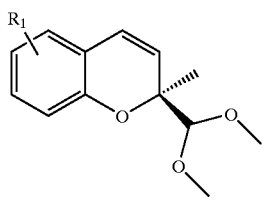

($V_2$)

Wherein $R_1$ is defined as above.

Olefin compound (V) can be prepared by the method disclosed in KR Pat. Appln. No. 96-7399 according to the present inventors. The following scheme 4 shows the detail process for the preparation of the olefin compound (V) from an alcohol compound (IV), prepared in scheme 3. The olefin compounds (V) can be obtained separately as an optically active olefin compound ($V_1$) and olefin compound ($V_2$) of formula 5, respectively.

SCHEME 4

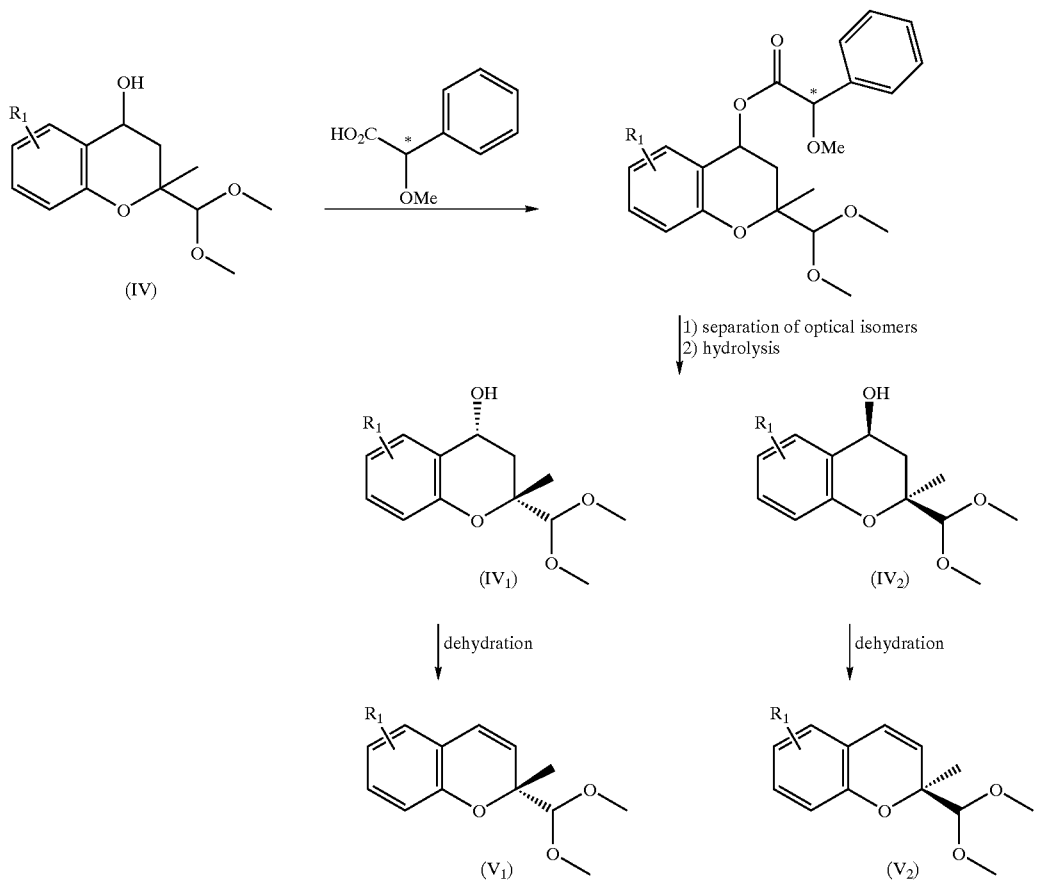

Wherein R₁ is defined as above.

(2) Preparation of Epoxide Compounds (II)

Epoxide compounds (II₁) and epoxide compounds (II₂) can be prepared from the compound (V₁) and epoxide compounds (II₃) and epoxide compounds (II₄) can be prepared from the compound (V₂) as represented by the following scheme 5, by using the compound (V₁) and the compound (V₂) prepared in scheme 4 as a starting material, respectively.

SCHEME 5

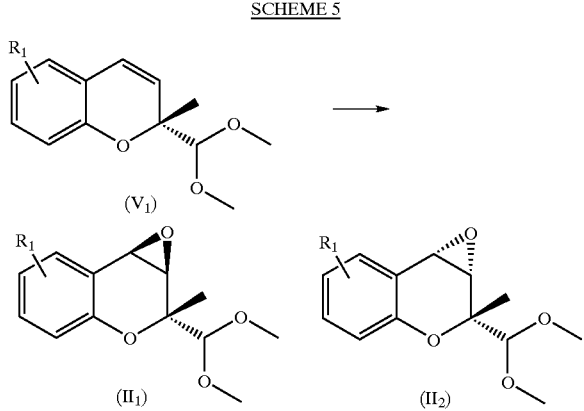

-continued

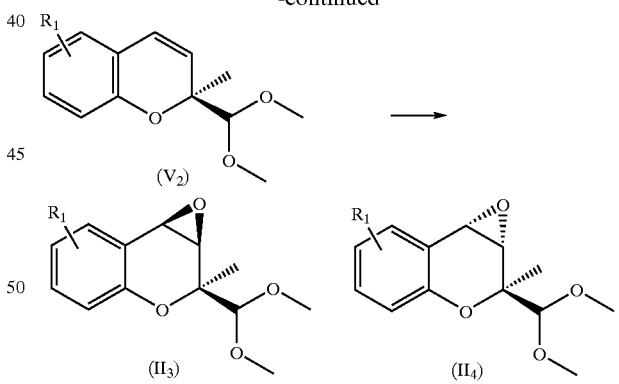

Wherein R₁ is defined as above.

The epoxide compounds (II₁) and (II₂) can be separated to each optical isomer, and all the separated epoxide compounds or the mixture thereof can be used in the next step. Also the epoxide compounds (II₃) and (II₄) can be separated, and all the separated epoxide compounds or the mixture thereof can be used in the next step.

Epoxide compounds (II₁) and (II₂) and epoxide compounds (II₃) and (II₄) can be prepared from olefin compounds (V₁) and (V₂), respectively, by the preparation method disclosed in U.S. Pat No. 5,236,935 and KR Pat. No. 096,546 which were acquired by the present inventors.

Also, the epoxide compound (II) can be prepared from propazylether derivatives [J. Med. Chem. 26, 1582 (1983)].

It is also possible to prepare optical isomers (II$_1$), (II$_2$), (II$_3$) and (II$_4$) of epoxide compounds, respectively, from olefin compounds (V$_1$) or (V$_2$), by using Mn(III) salen epoxidation catalysts [E. N. Jacobsen et al., Tetrahedron Lett., 38, 5055 (1991)]. In case of using (R,R)—Mn(III) salen catalyst, epoxide compounds (II$_1$) can be prepared from olefin compounds (V$_1$) and epoxide compounds (II$_3$) from the olefin compounds (V$_2$). In case of using (S,S)—Mn(III) salen catalyst, epoxide compounds (II$_2$) can be prepared from the olefin compounds (V$_1$) and epoxide compounds (II$_4$) from the olefin compounds (V$_2$). This epoxidation reaction is performed in co-solvent of methylene chloride and water by using NaOCl as an oxidizing agent.

(3) Preparation of Heterocycle Comopunds (III)

Heterocyclic amine compounds (III) which were used as a starting material in the above scheme 1, can be prepared from the selective reduction of aromatic hetero-ring compounds (VI) represented by following scheme 6.

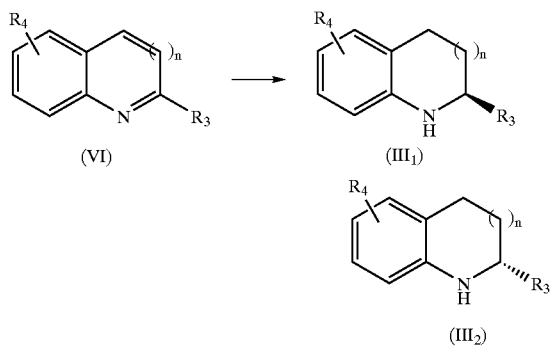

Wherein R$_3$, R$_4$, and n are each defined as above.

Hetero-rings such as pyrrole and pyridine in heterocyclic compounds (VI) can be selectively reduced through the hydrogenation reaction using the metal catalysts such as platinum, Raney-nickle, etc. Preferred solvents are alcohols such as methanol, ethanol, etc.

In the above scheme 6, indole compounds in which n is 0, can be reduced to indoline by using NaCNBH$_3$ as a reducing agent in trifluoroacetic acid. Reaction temperature may range from 0° C. to rt. In addition, magnesium turning in methanol can reduce the pyrrole ring of indole compounds.

In the above scheme 6, quinoline compounds in which n is 1, can be reduced by using NaCNBH$_3$ as a reducing agent in acidic pH, which has to be maintained as pH 4 using methanolic HCl in co-solvents of tetrahydrofuran, and methanol.

Amine compounds (III$_1$) and (III$_2$) can be separated to each optical isomer, and all the separated amine compounds or the mixture thereof can be used in next step. Optical isomers (III$_1$) and (III$_2$) can be separated by the reaction with enzymes such as hydrolases, or by the chromatography using chiral stationary column [W. H. Pirkle et al., J. of Chromatography, 316, 585 (1984)], or by the crystallization of salts with cinchonidine [J. L. Stanton et al., J. Med. Chem. 26, 1267 (1983)], etc., using different solubility between optical isomers.

In addition, optical isomer (III$_1$) and (III$_2$) can be synthesized separately by the chiral auxiliary mediated reduction of aromatic heterocycle compounds (VI) [A. V. Karchava et al., Tetrahedron: Asymmetry, 6, 2895 (1995)], by the chiral auxiliary mediated heterocyclic ring formation [J. P. Marino et al., J. Am. Chem. Soc. 114, 5566 (1992); A. I. Meyers et al., J. Org. Chem. 57, 3673 (1992)], or by the asymmetric substitution at 2-position of N-protected indoline compounds using chiral ligand [A. I. Meyers et al., J. Org. Chem. 58,6538 (1993); P. Beak et. Al., J. Org. Chem. 62, 7679 (1997)].

II. Preparation of Compound (II') from the Starting Compounds

The method for the preparation of compounds (formula 1) comprises the step of coupling an epoxide compound (II) and heterocyclic amine compound (III) in the presence of NaH, K$_2$CO$_3$, t-BuOK, Mg(ClO$_4$)$_2$, CoCl$_2$, etc. The compound (I'), which is a compound of formula 1 with R$_2$=OH and 2,3-single bond in heterocycles, is prepared by this reaction.

In case of using bases, preferable reaction solvent is ether such as tetrahydrofuran or substituted amide such as N,N-dimethylformamide, and in case of using metal salts, preferable solvent is acetonitrile. Reaction temperature may range from rt to boiling point of employed solvent.

In case of using each stereoisomer of the epoxide compound (II) and heterocyclic amine compounds (III) as a starting material, the product with the same configuration to that of the starting material is obtained, respectively. That is, the compounds (I$_8$) (I$_6$), (I$_1$) or (I$_3$) of formula 1 can be prepared from epoxide compounds (II$_1$), (II$_2$), (II$_3$) or (II$_4$) with amine compounds (III$_1$), respectively. And the compounds (I$_7$), (I$_5$), (I$_2$) or (I$_4$) of formula 4 can be prepared from epoxide compounds (II$_1$), (II$_2$), (II$_3$) or (II$_4$) with amine compounds (III$_2$), respectively. In case of using a stereoisomer of the epoxide compound (II$_1$), (II$_2$), (II$_3$) or (II$_4$), and a mixture of heterocyclic amine compounds (III) as a starting material, diastereomeric mixture of compounds (I$_8$) and (I$_7$), (I$_6$) and (I$_5$), (I$_1$) and (I$_2$), or (I$_3$) and (I$_4$) are obtained, respectively, which are separated by chiral column chromatography to give each stereoisomers.

III. Preparation of Compounds (I) from the Compounds (I')

For preparation of compound (I), the substituents R$_1$, R$_2$, R$_3$ and R$_4$ of the compound (I') can be modified to other functional groups, and a double bond can be introduced at 2,3-position of heterocycle by the reaction of scheme 2.

A starting material, reactants and the reaction condition are determined according to the structure of product, that is what are the substituents R$_1$, R$_2$, R$_3$, and R$_4$ and whether there is a double bond at 2,3-position of heterocycle. Therefore the present invention includes all the reaction types, reactants and reaction conditions by which it is possible to prepare the compound of formula 1.

Several processes for the preparation of the compounds of formula 1 according to scheme 2 are described below in detail. However, the description of the processes, reactants and reaction conditions should not be understood to limit the present invention.

(1) Introduction of Double Bond at 2, 3-position of Heterocycle

Benzopyranyl indole compounds (I$_b$) can be prepared from the coupling of epoxide compound (II) with indole amines (III$_b$) as represented in the below scheme 7, but whose yields are very low already reported [K. S. A. Atwal et al., *J. Med. Chem.*, 38, 3236 (1995)].

Scheme 7

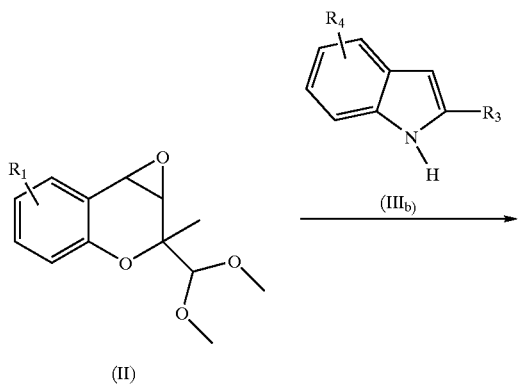

(II)

(III$_b$)

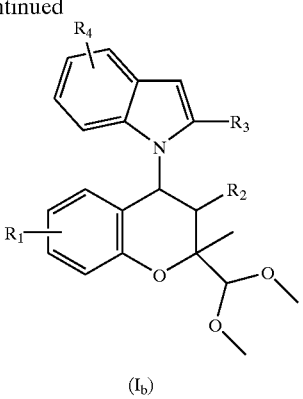

(I$_b$)

Wherein R$_1$, R$_2$, R$_3$ and R$_4$ are each defined as above.

The aromatization of indoline to indole can be carried out by using a oxidizing agent such as MnO$_2$, DDQ (2,3-dichloro-5,6-dicyano-1,4-benzoquinone), etc. In the case of using DDQ, the reaction is proceeded at rt, and preferable solvents are aromatic solvents such as benzene, toluene, etc., and ethers such as dioxane, etc.

(2) Introduction of NH$_2$ group at R$_1$

The compound (I$_c$) of formula 1 whose R$_1$ is NH$_2$ can be prepared by the reduction of the compound (I$_d$) with R$_1$=NO$_2$ as represented in the below scheme 9.

SCHEME 9

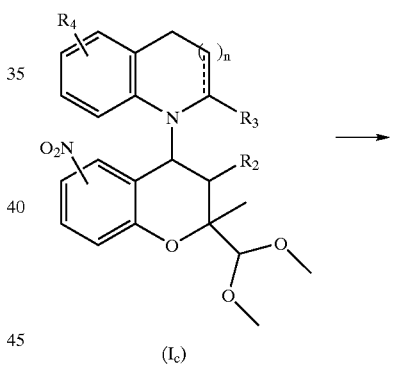

(I$_c$)

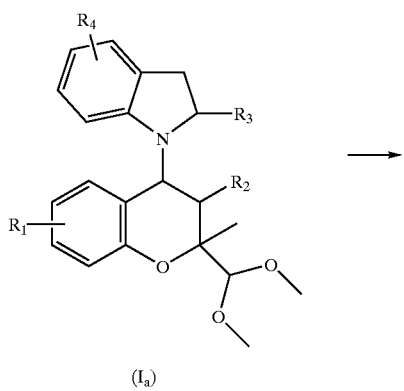

Wherein R$_1$, R$_2$, R$_3$ and R$_4$ are each defined as above.

Indoline compounds (I$_a$), of which n is 0, can be aromatized to indole compounds (I$_b$), which has a double bond at 2,3-position by oxidation as represented in the below scheme 8. Then, Aromitization of indoline compounds (around 80% yield) is more preferable to prepare benzopyranyl indole compounds (I$_b$).

Scheme 8

(I$_a$)

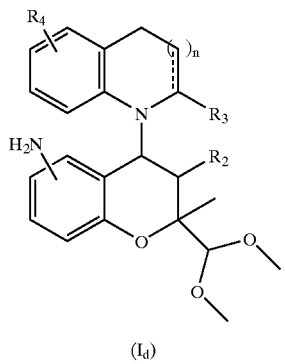

(I$_d$)

Wherein R$_2$, R$_3$, R$_4$ and n are each defined as above.

The NO$_2$ group can be reduced to NH$_2$ group by hydrogenation using metal catalysts such as platinum, palladium, palladium on carbon (Pd/C), Raney-nickel, etc. in a suitable solvent. Preferred solvents are alcohols such as methanol, ethanol, etc., and ethyl acetate.

In addition, the reduction of $NO_2$ group to $NH_2$ group can be carried out by using a reducing agent such as $NaBH_4$ in the presence of $CuSO_4$, $Cu(OAc)_2$, $CoCl_2$, $SnCl_2$ or $NiCl_2$. At this time, preferred solvent is a mixture of water and methanol, and room temperature for reaction temperature is preferred.

(3) Lactone Ring Formation by the Intramolecular Esterification

The lactone compound ($I_f$) of formula 1 can be prepared by the intramolecular esterification of the compound ($I_e$) with $R_3=C(=O)OR^a$ as represented in the below scheme 10.

Scheme 10

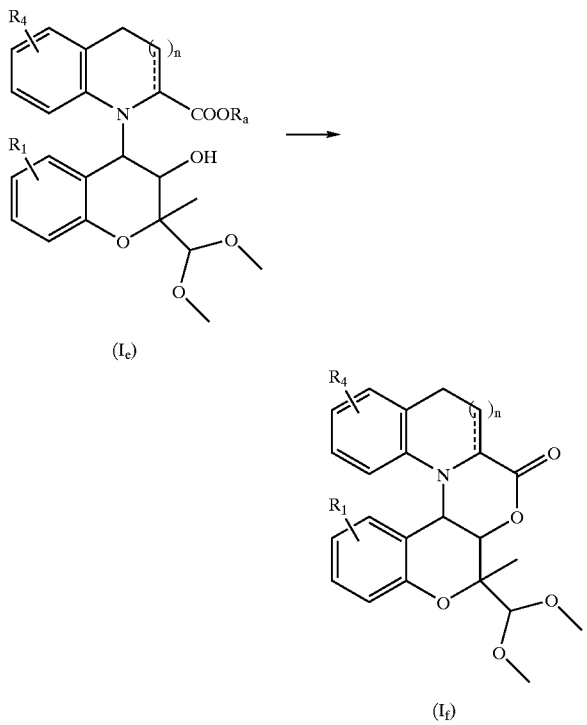

Wherein $R_2$, $R_4$, $R^a$ and n are each defined as above.

In the case of using the carboxylic acid compound with $R^a=H$ as a starting material, the lactone compound ($I_f$) can be prepared by activating to mixed anhydride with alkyl formate or to azide with diphenylphosphoryl azide, etc., or by condensing using N,N'-dicyclohexylcarbodiimide (DCC), water-soluble carbodiimidazole (WSC), etc. Preferable solvents are ether type such as tetrahydrofuran, etc., and substituted amide such as N,N-dimethylformamide, etc.

In the case of using the carboxylic ester compound with $R^a$=alkyl or aryl as a starting material, the lactone compound ($I_f$) can be prepared using Lewis acid such as diethylchloro aluminum etc., in the presence of base catalyst such as diisopropylamine, etc. Preferable solvent is $CH_2Cl_1$, etc.

(4) Introduction of

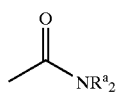

to $R_3$

The amide compound ($I_g$) whose $R_3$ is

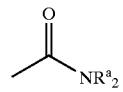

can be prepared by the aminolysis of the compound ($I_e$) with $R_3=C(=O)OR^a$ or by the coupling of the heterocyclic amide compound ($III_g$) with epoxide (II), as represented in the below scheme 11.

Scheme 11

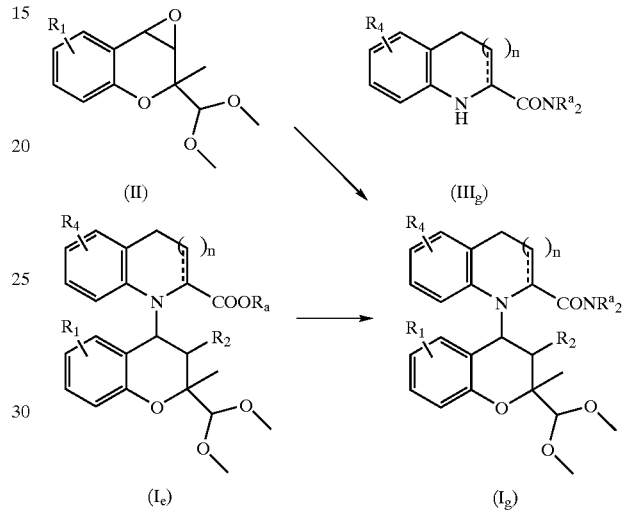

Wherein $R_1$, $R_2$, $R_4$, $R^a$ and n are each defined as above.

Preferable solvent for aminolysis is alcohol such as methanol, ethanol, etc.

The molecular structure of the compounds according to the present invention was identified by IR spectroscopy, UV spectroscopy, NMR spectroscopy, mass spectroscopy, liquid chromatography, X-ray diffraction, optical rotation analysis and elemental analysis.

In addition, the present invention provides pharmaceutical compositions which contain the benzopyranyl heterocycle derivatives of the above formula 1 or their pharmaceutically acceptable salts as an active ingredient. In particular, the present invention provides pharmaceutical compositions for protecting heart, protecting neuronal cells, protecting from brain injury, or suppressing lipid peroxidation.

In the experiments using isolated rat aorta, the compounds of the present invention showed remarkably low vasorelaxant activity compared to the reference $K_{ATP}$ openers such as Cromakalim and BMS-180448. The $K_{ATP}$ openers usually have both cardioprotective and vasodilating properties, and those are reported not to have correlation between them [K. S. Atwal et al., J. Med. Chem. 39, 304 (1996)]. The vasodilation effect is unnecessary, probably contraindicated for ischemia, due to underperfusion of the tissue already at risk. In other words, the vasorelaxant effect of these compounds would limit their utility in treating myocardial ischemia. As mentioned above, the compounds of the present invention are nearly devoid of vasorelaxant activity, thus their cardiac selectivity might offer a higher margin of safety as cardioprotectants.

Accordingly, the compounds of the present invention are confirmed their antiischemic activity with significant improvement in cardiac selectivity. In isolated ischemic rat heart model using Langendorff apparatus, the compounds of the present invention significantly prolong the time to contracture (TTC), improve the recovery of postischemic contractile function, and decrease the release of lactate dehydrogenase (LDH) which is a marker enzyme for cell injury. In the ischemic myocardium injury models of anesthetized rats, the compounds of the present invention exhibited equal or superior antiischemic activity compared to that of BMS-180448. Further, in contrast to BMS-180448, the compounds of the present invention have noticeably low vasorelaxant activity and thus, they are superior to the conventional drugs as cardiac selective cardioprotectants.

As described above, the compounds of the present invention exert excellent anti-ischemic activity both in vitro and in vivo, while show low vasorelaxant acitivity, so that they can be used for the prevention or treatment of the diseases related to myocardial ischemia, such as postischemic contractile dysfunction, myocardial cell injury, and change of energy metabolism as well as a cardioprotective.

In addition, the compounds of the present invention have an ability to protect neurons. In detail, the compounds of the present invention protect neurons from oxidative stress by iron. Therefore, the compounds of the present invention can be used as a neuroprotective and can also be applied for the treatment of neurodegenerative disorders caused by the apoptosis or necrosis of neurons, such as stroke and cerebral dementia.

Further, the compounds of the present invention inhibit the lipid peroxidation induced by iron. Hence, the compounds of the present invention can be used as an antioxidant against lipid peroxidation and can be effectively applied for the medical treatment of the neurological disorders caused by the accumulation of free radical species within neurons, such as a stroke and dementia.

The present invention includes pharmaceutical formulations which contain, in addition to non-toxic, inert pharmaceutically suitable additives, one or more than one active ingredients according to the present invention and processes for the preparation of these formulations.

Non-toxic inert pharmaceutically suitable vehicle include solid, semi-solid or liquid diluents, fillers and formulation additives of all types.

Preferred pharmaceutical formulations are tablets, coated tablets, capsules, pills, granules, suppositories, solutions, suspensions and emulsions, pastes, ointments, gels, creams, lotions, dusting powders and sprays.

Tablets, coated tablets, capsules, pills and granules can contain the more than one additives in addition to the active ingredient or ingredients, such as (a) fillers and diluents, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrants, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate, and solid polyethylene glycols, or mixtures of the substances listed under (a) to (i).

The tablets, coated tablets, capsules, pills and granules can be provided with the customary coatings and shells, optionally containing opacifying agents, and can also be of a composition such that they release the active ingredient or ingredients only or preferentially in a certain part of the intestinal tract, if appropriate in a delayed manner, examples of embedding compositions which can be used being polymeric substances and waxes.

If appropriate, the active ingredient or ingredients can also be present in microencapsulated form with one or more of the above mentioned excipients.

Suppositories can contain, in addition to the active ingredient or ingredients, the customary water-soluble or water-insoluble excipients, for example polyethylene glycols, fats, for example cacao fat, and higher esters (for example, $C_{14}$-alcohol with $C_{16}$-fatty acid) or mixtures of these substances.

Ointments, pastes, creams and gels can contain, in addition to the active ingredient or ingredients, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Dusting powders and sprays can contain, in addition to the active ingredient or ingredients, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active ingredient or ingredients, the customary excipients, such as solvents, solubilizing agents and emulsifiers, for example water, ethyl alcohol, isopropyl alcohol, ethylcarbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuyl alcohol, polyethylene glycols and fatty acid esters of sorbitan, or mixtures of these substances.

For parenteral administration, the solutions and emulsions are also be in a sterile form which is isotonic with blood.

Suspensions can contain, in addition to the active ingredient or ingredients, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain coloring agents, preservatives and additives which improve the smell and taste, for example peppermint oil and eucalyptus oil, and sweeteners, for example saccharin.

The therapeutically active ingredients should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the present invention.

The abovementioned pharmaceutical formulations are prepared in the customary manner by known methods, for example by mixing the active ingredient or ingredients with vehicles.

The formulations mentioned can be used on humans and animals either orally, rectally, parenterally (intravenously, intramuscularly or subcutaneously), intracisternally, intravaginally, intraperitoneally or locally (dusting powder, ointment, drops) and for the therapy of infections in hollow spaces and body cavities. Possible suitable formulations are injection solutions, solutions and suspensions for oral therapy and gels, infusion formulations, emulsions, ointments or drops, ophthalmological and dermatological formulations, silver salts and other salts, eardrops, eye onintments, dusting powders or solutions can be used for local therapy. In the case of animals, intake can also be in suitable formulations via the feed or drinking water.

Gels, powders, dusting powders, tablets, delayed release tablets, premixes, concentrates, granules, pellets, capsules, aerosols, sprays and inhalants can furthermore be used on humans and animals. The compounds according to the present invention can moreover be incorporated into other carrier materials, such as for example, plastics (chain of plastic for local therapy), collagen or bone cement.

In general, it has proved advantageous both in human medicine to administer the active compound or compounds according to the present invention in total amounts of about 0.1 to about 100, preferably 0.1 to 20 mg/kg of body weight every 24 hours, if appropriate in the form of several individual doses, to achieve the desired results. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place.

Thus in some cases it can suffice to manage with less than the abovementioned amount of active ingredient, while in other cases the abovementioned amount of active ingredient must be exceeded. The particular optimum dosage and mode of administration required for the active ingredient can be determined by any expert on the basis of his expert knowledge.

Preparation Examples

The starting materials, (II) and (III) of scheme 1 or scheme 2 were prepared from the following preparation examples.

Preparation Example 1

Preparation of (2S, 3R, 4R)-3,4-dihydro-2-dimethoxymethyl-3,4-epoxy-2-methyl-6-nitro-2H-1-benzopyran To the pre-cooled solution of 0.55 M NaOCl (110 mL, 60.0 mmol) and 0.05 M $Na_2HPO_4$ (43 mL) at 0° C., was added (2S)-2-dimethoxymethyl-2-methyl-6-nitro-2H-1-benzopyran (4 g, 15 mmol) and (R,R) Jacobson's catalyst (477.5 mg, 0.75 mmol) in $CH_2Cl_2$ (20 mL). The reaction mixture was stirred at rt for 8 hr and then filtered through Celite to remove the jacobson's catalyst. The layer was separated and the organic layer was washed with brine, dried ($Na_2SO_4$), filtered, then concentrated under reduced pressure. The residue was purified by silicagel column chromatography (n-hexane:ethyl acetate=4:1) to give the desired compound (3.24 g, 77%) as a light yellow solid.

$^1$H NMR (CDCl$_3$, 200 MHz) δ1.28 (s, 3H), 3.60 (s, 3H), 3.67 (s, 3H), 3.80 (d, 1H), 3.96 (d, 1H), 4.47 (s, 1H), 6.94 (d, 1H), 8.15 (dd, 1H), 8.30 (d, 1H)

Preparation Example 2

Preparation of (2S, 3S, 4S)-3,4-dihydro-2-dimethoxymethyl-3,4-epoxy-2-methyl-6-nitro-2H-1-benzopyran The reaction was proceeded by the same method used for the preparation example 1 above, except using (S,S) Jacobson's catayst. The residue was purified by column chromatography (n-hexane:ethyl acetate=4:1) to give the desired compound (3.81 g, 90%) as a light yellow solid.

$^1$H NMR (CDCl$_3$, 200 MHz) δ1.56 (s, 3H), 3.28 (s, 3H), 3.49 (s, 3H), 3.82 (d, 1H), 4.11 (d, 1H), 4.22 (s, 1H), 6.85 (d, 1H), 8.13 (dd, 1H), 8.27 (d, 1H)

Preparation Example 3

Preparation of (2R, 3S,4S)-3,4-dihydro-2-dimethoxymethyl-3,4-epoxy-2-methyl-6-nitro-2H-1-benzopyran To the pre-cooled solution of 0.55 M NaOCl (55 mL, 30.0 mmol) and of 0.05 M $Na_2HPO_4$ (21.5 mL) at 0° C., (2R)-2-dimethoxymethyl-2-methyl-6-nitro-2H-1-benzopyran n(2 g, 7.5 mmol) and (R, R) Jacobson's catalyst (477.5 mg, 0.75 mmol) in $CH_2Cl_2$ (10 mL) was added. The reaction mixture was stirred at rt for 8 hr and then filtered through Celite to remove the jacobson's catalyst. The layer was separated and the organic layer was washed with brine, dried ($Na_2SO_4$), filtered, then concentrated under reduced pressure. The residue was purified by silicagel column chromatography (n-hexane:ethyl acetate=4:1) to give the desired compound (1.64 g, 77%) as a light yellow solid.

$^1$H NMR (CDCl$_3$, 200 MHz) δ1.28 (s, 3H), 3.60 (s, 3H), 3.67 (s, 3H), 3.80 (d, 1H), 3.96 (d, 1H), 4.47 (s, 1H), 6.94 (d, 1H), 8.15 (dd, 1H), 8.30 (d, 1H)

Preparation Example 4

Preparation of (2R, 3R,4R)-3,4-dihydro-2-dimethoxymethyl-3,4-epoxy-2-methyl-6-nitro-2H-1-benzopyran The reaction was proceeded by the same method used for the preparation example 3 above, except using (R,R) Jacobson's catalyst. The residue was purified by column chromatography (n-hexane:ethyl acetate=4:1) to give the desired product (1.55 g, 78%) as a light yellow solid.

$^1$H NMR (CDCl$_3$, 200 MHz) δ1.56 (s, 3H), 3.28 (s, 3H), 3.49 (s, 3H) 3.82 (d, 1H), 4.11 (d, 1H), 4.22 (s, 1H) 6.85 (d, 1H), 8.13 (dd, 1H), 8.27 (d, 1H)

Preparation Example 5

Preparation of 2,3-Dihydro-1H-indole-2-carboxylic acid ethyl ester

To cooled trifluoroacetic acid (40 mL) at 0° C., NaCNBH$_3$ (1.57 g, 25 mmol) was added portionwise with stirring. The reaction mixture was stirred for 15 min, and to which indole-2-carboxylic acid ethyl ester (1.2 g, 6.35 mmol) was added slowly, then the mixture was stirred at rt for an hour. After the completion of the reaction, water (150 mL) was added to the mixture, and which was stirred for 5 hr. The reaction was extracted by $CH_2Cl_2$ (40 mL×3), then organic layer was washed with saturated aqueous solution of NaHCO$_3$ (40 mL×2) and water (40 mL), dried (Na$_2$SO$_4$), filtered, and concentrated under reduced pressure. The residue was purified by silica gel column chromatography (n-hexane:ethyl acetate=9:1) to give the desired compound (1.09 g, 90%).

$^1$H NMR (CDCl$_3$, 200 MHz) δ1.29 (t, 3H), 3.34 (m, 2H), 4.07 (bs, 1H), 4.20 (q, 2H), 4.36 (dd, 1H), 6.74 (m, 2H), 7.08 (m, 2H)

Preparation Example 6

Preparation of 2,3-Dihydro-1H-5-fluoroindole-2-carboxylic acid ethyl ester (Step 1) Preparation of 5-fluoroindole-2-carboxylic acid ethyl ester To the solution of 5-fluoroindole-2-carboxylic acid (1.0 g, 5.58 mmol) in DMF (10,0 mL), was added K$_2$CO$_3$ (1.0 g, 7.80 mmol), followed by bromoethane (685 mg, 6.29 mmol) dropwise at 0° C. After the reaction mixture was stirred at rt for 10 hr, water (30 mL) was added to the reaction mixture, which was extracted with ethyl acetate (15 mL×3). The organic layer was washed with brine and water, dried ($Na_2SO_4$), filtered and concentrated under reduced pressure to give the desired product (820 mg, 71%), which was used for the next step without further purification.

$^1$H NMR ($CDCl_3$, 200 MHz) δ1.42 (t, 3H), 4.43 (q, 2H), 7.08 (ddd, 1H), 7.18 (s, 1H), 7.38 (m, 2H), 9.34 (bs, 1H)

(step 2) Preparation of 2,3-Dihydro-1H -5-fluoroindole-2-carboxylic acid ethyl ester To cooled trifluoroacetic acid (15 mL) at 0° C., $NaCNBH_3$ (730 mg, 11.6 mmol) was added portionwise with stirring. The reaction mixture was stirred for 15 min, and to which the compound obtained from step 1 (600 mg, 2.90 mmol) was added slowly, then the mixture was stirred at rt for an hour. After the completion of reaction, water (150 mL) was added to the mixture, which was stirred for 5 hr. The reaction was extracted by $CH_2Cl_2$ (20 mL×3), then organic layer was washed with saturated aqueous solution of $NaHCO_3$ (20 mL×2) and water (20 mL), dried ($Na_2SO_4$), filtered, and concentrated under reduced pressure. The residue was purified by silica gel column chromatography (n-hexane:ethyl acetate=9:1) to give the desired compound (605 mg, 63%)

$^1$H NMR ($CDCl_3$, 200 MHz) δ1.29 (t, 3H), 3.32 (m, 2H), 4.25 (q, 2H), 4.39 (m, 1H), 6.62 (ddd, 1H), 6.79 (m, 2H)

Preparation Example 7

Preparation of 2,3-Dihydro-1H-5-chloroindole-2-carboxylic acid ethyl ester

To cooled trifluoroacetic acid (15 mL) at 0° C., $NaCNBH_3$ (1.50 mg, 23.87 mmol) was added portionwise with stirring. The reaction mixture was stirred for 15 min, and to which 5-chloroindole-2-carboxylic acid ethyl ester (1.0 g, 4.47 mmol) was added slowly, then the mixture was stirred at rt for an hour. After the completion of reaction, water (150 mL) was added to the mixture, which was stirred for 5 hr. The reaction was extracted by $CH_2Cl_2$ (40 mL×3), then organic layer was washed with saturated aqueous solution of $NaHCO_3$ (40 mL×2) and water (40 mL), dried ($Na_2SO_4$), filtered, and concentrated under reduced pressure. The residue was purified by silica gel column chromatography (n-hexane:ethyl acetate=9:1) to give the desired compound (870 mg, 87%)

$^1$H NMR ($CDCl_3$, 200 MHz) δ1.29 (t, 3H), 3.35 (m, 2H), 4.24 (q, 2H), 4.37 (dd, 1H), 6.62 (d, 1H), 7.03 (m, 2H)

Preparation Example 8

Preparation of 2,3-Dihydro-1H-5-methoxyindole-2-carboxylic acid ethyl ester (Step 1) Preparation of 1H-5-methoxyindole-2-carboxylic acid ethyl ester Except using 5-methoxyindole-2-carboxylic acid (1.0 g, 5.23 mmol) as a starting material, the reaction was proceeded by the same method used for the step 1 of preparation example 6 above, which gave the desired product (985 mg, 86%).

$^1$H NMR ($CDCl_3$, 200 MHz) δ1.41 (t, 3H), 3.85 (s, 3H), 4.40 (q, 2H), 7.01 (dd, 1H), 7.07 (s, 1H), 7.14 (d, 1H), 7.29 (d, 1H), 8.82 (bs, 1H)

(Step 2) Preparation of 2,3-dihydro-1H-5-methoxyindole-2-carboxylic acid ethyl ester Except using the compound (985 mg, 4.50 mmol) prepared from step 1 as a starting material, the reaction was proceeded by the same procedure used for the step 2 of preparation example 6 above. The residue was purified by silica gel column chromatography (n-hexane:ethyl acetate=9:1) to give the desired compound (624 mg, 63%).

$^1$H NMR ($CDCl_3$, 200 MHz) δ1.28 (t, 3H), 3.31 (m, 2H), 3.73 (s, 3H), 4.20 (q, 2H), 4.36 (dd, 1H),6.63 6.72 (m, 3H)

Preparation Example 9

Preparation of 2,3-Dihydro-1H-5-indole-2-carboxylic acid methyl ester

To the solution of indole-2-carboxylic acid ethyl ester (1.4 g, 8 mmol) in anhydrous methanol (40 mL), magnesium turnings (1.84 g, 80 mmol) were added portionwise with stirring. The reaction mixture was continuously stirred at 10–15° C. until magnesium was completely dissolved, then poured onto the precooled an aqueous solution of 2N HCl at 4° C. The reaction was basified to pH 9 with ammonia water, and extracted with ethyl acetate (20 mL×3). The organic layer was washed with water (40 mL), dried ($Na_2SO_4$), dried, and concentrated under reduced pressure. The residue was purified by silica gel column chromatography (n-hexane:ethyl acetate=9:1) to give the desired compound (1.20 g, 85%).

$^1$H NMR ($CDCl_3$, 200 MHz) δ3.34 (m, 2H), 3.74 (s, 3H), 4.21 (m, 1H), 6.75 (m, 2H), 7.06 (m, 2H)

Preparation Example 10

Preparation of 2,3-Dihydro-1H-5-chloroindole-2-carboxylic acid methyl ester

Except using 5-chloroindole-2-carboxylic acid ethyl ester (3.0 g, 13.4 mmol) as a starting material, the reaction was proceeded by the same method used for the preparation example 9 above. The residue was purified by silica gel column chromatography (n-hexane:ethyl acetate=9:1) to give the desired compound (2.21 g, 78%).

$^1$H NMR ($CDCl_3$, 200 MHz) δ3.36 (m, 2H), 3.79 (s, 3H), 4.43 (m, 1H), 6.64 (d, 1H), 7.04 (d, 2H)

Preparation Example 11

Preparation of 2,3-Dihydro-1H-5-chloro-2-hydroxymethylindole (Step 1) Preparation of 2,3-Dihydro-1H-5-chloroindole-2-carboxylic acid The compound (1.2 g, 5.67 mmol) obtained from preparation example 10 above, was dissolved in methanol (15 mL), to which was added KOH (57 mg, 6.14 mmol) in water (0.3 mL) . The reaction mixture was stirred at rt for 3 hr, then all volatiles were removed under reduced pressure. Water (10 mL) was added to the residue, which was acidified to pH 3 with c-HCl, and extracted with ethyl acetate (10 mL×3). The extracts were dried ($Na_2SO_4$), filters and concentrated under reduced pressure to give the desired compound (1.01 g, 90%), which was used for the next step without further purification.

$^1$H NMR ($CD_3OH$, 200 MHz) δ3.34 (m, 2H), 4.38 (dd, 1H), 6.61 (d, 1H), 6.93 (dd, 1H), 7.02 (d, 1H)

(Step 2) Preparation of 2,3-Dihydro-1H-5-chloro-2-hydroxymethylindole

To the precooled solution of the compound (198 mg, 1.0 mmol) obtained from step 1 in dry THF (2 mL) at 0° C., 1N BH$_3$ in THF (2.5 mL) was added dropwise via a syringe. The reaction mixture was stirred at rt for 5 hr, then concentrated in vacuo. To the residue water (5 mL) was added, which was extracted with ethyl acetate (5 mL×3). The extracts were washed with saturated aqueous solution of NaHCO$_3$, brine, and water, dried (Na$_2$SO$_4$), filtered, and concentrated under reduced pressure. The residue was purified by silica gel column chromatography (n-hexane:ethyl acetate=4:1) to give the desired compound (167 mg, 91%).

$^1$H NMR (CDCl$_3$, 200 MHz) δ2.82 (dd, 1H), 3.11 (dd, 1H), 3.64 (m, 2H), 4.04 (m, 1H), 6.55 (d, 1H), 7.02 (m, 2H)

Preparation Example 12

Preparation of (2S)-2,3-Dihydro-1H-indole-2-carboxylic acid isopropyl ester

To the solution of (2S)-2,3-dihydroindole-2-carboxylic acid (163 mg, 1.0 mmol) in isopropyl alcohol (40 mL), was added thionyl chloride (0.1 mL) slowly. The reaction mixture was heated at reflux for 4 hr with stirring. After cooling, all volatiles were removed under reduced pressure. To the residue saturated aqueous solution of NaHCO$_3$ (10 mL) was added, which was extracted with ethyl acetate (10 mL×3). The extracts were dried (Na$_2$SO$_4$), filtered, and concentrated under reduced pressure. The residue was purified by silica gel column chromatography (n-hexane:ethyl acetate=4:1) to give the desired compound (182 mg, 89%).

$^1$H NMR (CDCl$_3$, 200 MHz) δ1.25 (s, 3H), 1.28 (s, 3H), 3.28 (m, 2H), 4.48 (dd, 2H), 5.05 (q, 1H), 6.89 (m, 2H), 7.10 (m, 2H)

Preparation Example 13

Preparation of 1,2,3,4-tetrahydro-1H-quinoline-2-carboxylic acid methyl ester (Step 1) Preparation of 1H-quinoline-2-carboxylic acid methyl ester To the solution of quinoline-2-carboxylic acid (500 mg, 2.89 mmol) in DMF (5 mL), K$_2$CO$_3$ (600 mg, 4.33 mmol) and iodomethane (412 mg, 2.9 mmol) were added at 0° C., and the reaction mixture was stirred at rt for 3 hr. Water (20 mL) was added to the mixture, which was extracted with ethyl acetate (10 mL×3). The extracts were dried (Na$_2$SO$_4$), filtered and concentrated under reduced pressure. The residue was purified by silica gel column chromatography (n-hexane:ethyl acetate 9:1) to give the desired compound (414 mg, 77%).

$^1$H NMR (CDCl$_3$, 200 MHz) δ4.08 (s, 3H), 7.61–7.92 (m, 3H), 8.18–8.38 (m, 3H)

(Step 2) Preparation of 1,2,3,4-tetrahydro-1H-quinoline-2-carboxylic acid methyl ester To the solution of the compound (540 mg, 2.9 mmol) obtained from step 1 in THF (10 mL) and methanol (5 mL), were added NaCNBH$_3$ (750 mg, 12 mmol) and bromocresol as an indicator, followed by methanolic HCl until yellow color was persistent. The reaction mixture was stirred at rt for 4 hr, then poured onto iced-water, and basified with NaHCO$_3$, which was extracted with ethyl acetate (10 mL×3). The extracts were dried (Na$_2$SO$_4$), filtered, concentrated under reduced pressure. The residue was purified by silica gel column chromatography (n-hexane:ethyl acetate= 9:1) to give the desired compound (484 mg, 88%).

$^1$H NMR (CDCl$_3$, 200 MHz) δ2.03 (m, 1H), 2.27 (m, 1H), 2.79 (m, 2H), 3.78 (s, 3H), 4.06 (dd,1H), 6.63 (dd, 2H), 6.97 (dd, 2H)

EXAMPLE 1

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester The mixture of the indoline compound (382 mg, 2 mmol) obtained from preparation example 5, (2S, 3R,4R)-epoxide (562 mg, 2 mmol) obtained from preparation example 1, and magnesium perchlorate (446.5 mg, 2 mmol) in CH$_3$CN (1 mL) was stirred at rt for 8 hr, then concentrated under reduced pressure. The residue was purified by silica gel column chromatography (n-hexane ethyl acetate=4:1) to give the desired compound (355 mg, 38%), having (2S, 3R, 4S, 2'R) stereochemistry.

$^1$H NMR (CDCl$_3$, 200 MHz) δ1.32 (t, 3H), 1.60 (s, 3H), 3.16 (m, 1H), 3.28 (s, 3H), 3.47 (s, 3H), 3.62 (m, 1H), 4.32 (q, 2H), 4.56 (m, 1H), 4.88 (m, 1H), 5.21 (s, 1H), 5.74 (d, 1H), 6.54 (dd, 1H), 6.70 (m, 1H), 6.91 (m, 1H), 7.08 (m, 2H), 7.58 (d, 0.6H), 7.95 (dd, 1H), 8.24 (d, 0.4H)

EXAMPLE 2

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester The same procedure as the preparation of example 1 was employed to give the desired compound (380 mg, 40%), having (2S, 3R, 4S, 2'S) stereochemistry.

$^1$H NMR (CDCl$_3$, 200 MHz) δ1.36 (m, 3H), 1.56 (s, 3H), 3.36 (m, 2H), 3.46 (s, 3H), 3.56 (s, 3H), 4.34 (q, 2H), 4.62 (d, 1H), 5.15 (dd, 1H), 5.60 (d, 1H), 6.62 (dd, 1H), 6.74 (m,1H), 6.84 (d, 1H), 7.08 (m, 2H), 7.8 (d, 0.4H), 8.08 (dd, 1H), 8.9 (d, 0.6H)

EXAMPLE 3

Preparation of 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester The mixture of the indoline compound (382 mg, 2 mmol) obtained from preparation example 5, (2S, 3S, 4S)-epoxide (562 mg, 2 mmol) obtained from preparation example 2, and magnesium perchlorate (446.5 mg, 2 mmol) in CH$_3$CN (1 mL) was stirred at rt for 3 hr, then concentrated under reduced pressure. The residue was purified by silica gel column chromatography (n-hexane:ethyl acetate=4:1) to give the desired compound (400 mg, 42%), having (2S, 3S, 4R, 2'R) stereochemistry.

$^1$H NMR (CDCl$_3$, 200 MHz) δ1.35 (m, 6H), 3.28 (m, 2H), 3.55 (s, 3H), 3.62 (s, 3H), 4.35 (q, 2H), 4.80 (m, 1H), 5.16 (m, 1H), 5.61 (d, 1H), 6.62 (dd, 1H), 6.80 (m, 1H), 6.94 (d, 1H), 7.10 (m, 2H) 7.82 (d, 0.6H), 8.08 (m, 1H), 8.90 (d, 0.4H)

EXAMPLE 4

Preparation of 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester The same procedure as the preparation of example 4 was employed to give the desired compound (412 mg, 44%), having (2S, 3S, 4R, 2'S) stereochemistry.

¹H NMR (CDCl₃, 200 MHz) δ1.35 (m, 6H), 3.38 (m, 2H), 3.64 (s, 3H), 3.66 (s, 3H), 4.29 (q, 2H), 4.68 (m, 1H) 4.91 (m, 1H), 5.22 (s, 1H), 5.38 (d, 1H), 6.61 (m, 1H), 6.72 (m, 1H), 6.84 (dd, 1H), 7.07 (m, 2H), 7.68 (d, 0.6H), 8.02 (m, 1H), 8.34 (d, 0.4H)

EXAMPLE 5

Preparation of 1-[(2S, 3R, 4S)-3,4-dihydro-2-dimethoxymethyl-3-hydroxy-2-methyl-6-nitro-2H-1-benzopyran-4-yl]-1H-(2R)-2,3-dihydroindole-2-carboxylic acid methyl ester The mixture of the indoline compound (470 mg, 2.65 mmol) obtained from preparation example 9, (2S, 3R,4R)-epoxide (562 mg, 2 mmol) obtained from preparation example 1, and magnesium perchlorate (610 mg, 2.7 mmol) in CH₃CN (1.5 mL) was stirred at rt for 8 hr, then concentrated under reduced pressure. The residue was purified by silica gel column chromatography (n-hexane:ethyl acetate= 4:1) to give the desired compound (488 mg, 40%), having (2S, 3R, 4S, 2'R) stereochemistry.

¹H NMR (CDCl₃, 200 MHz) δ1.64 (s, 3H), 3.10–3.60 (m, 8H), 3.95 (s, 3H), 4.58 (m, 1H), 4.85–5.16 (m, 2H), 5.79 (d, 1H), 6.46 (dd, 1H), 6.60 (m, 1H), 6.91 (m, 1H), 7.06 (m, 2H), 7.64 (d, 0.4H), 8.04 (m, 1H), 8.31 (d, 0.6H)

EXAMPLE 6

Preparation of 1-[(2S, 3R, 4S)-3,4-dihydro-2-dimethoxymethyl-3-hydroxy-2-methyl-6 -nitro-2H-1-benzopyran-4-yl]-1H-(2S)-2,3-dihydroindole-2-carboxylic acid methyl ester The same procedure as the preparation of example 5 was employed to give the desired compound (542 mg, 45%), having (2S, 3R, 4S, 2'S) stereochemistry.

¹H NMR (CDCl₃, 200 MHz) δ1.62 (s, 3H), 3.38 (m, 2H).3.64 (s, 3H), 3.67 (s, 3H), 3.89 (s, 3H), 4.41 (m, 1H), 4.62 (m, 1H), 5.06 (s, 1H), 5.52 (d, 1H), 6.63 (dd, 1H), 6.72 (m, 1H), 6.81 (d, 1H), 6.92 (m, 1H), 7.64 (d, 1H), 8.08 (m, 1H), 8.26 (d, 0.3H), 8.81 (d, 0.7H)

EXAMPLE 7

Preparation of 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid methyl ester The mixture of the indoline compound (600 mg, 3.39 mmol) obtained from preparation example 9, (2S, 3S,4S)-epoxide (952 mg, 3.39 mmol) obtained from preparation example 2, and magnesium perchlorate (760 mg, 3.4 mmol) in CH₃CN (1.5 mL) was stirred at rt for 3 hr, then concentrated under reduced pressure. The residue was purified by silica gel column chromatography (n-hexane:ethyl acetate= 4:1) to give the desired compound (490 mg, 32%), having (2S, 3S, 4R, 2'R) stereochemistry.

¹H NMR (CDCl₃, 200 MHz) δ1.32 (s, 3H), 3.28 (m, 2H), 3.54 (s, 3H), 3.61 (s, 3H), 3.86 (s, 3H), 4.41 (m, 1H), 4.79 (d, 1H), 5,11 (m,1H), 5.59 (d, 1H), 6.60–7.20 (m, 5H), 7.81 (d, 0.4H), 8.08 (m, 1H), 8.84 (d, 0.6H)

EXAMPLE 8

Preparation of 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid methyl ester The same procedure as the preparation of example 7 was employed to give the desired compound (490 mg, 32%), having (2S, 3S, 4R, 2'S) stereochemistry.

¹H NMR (CDCl₃, 200 MHz) δ1.57 (s, 3H), 3.26 (m, 1H), 3.46 (m, 1H), 3.64 (s, 3H), 3.68 (s, 3H), 3.89 (s, 3H), 4.30 (m, 1H), 4.60 (s, 1H), 4.69 (d, 1H), 4.91 (m, 1H), 6.63 (m, 1H), 6.72 (m, 1H), 6.94 (m, 1H), 7.08 (m, 2H), 7.68 (d, 0.3H), 8.01 (dd, 1H), 8.39 (d, 0.7H)

EXAMPLE 9

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid The solution of the compound (170 mg, 0.36 mmol) obtained from example 2 in methanol (3 mL) and 1N aqueoys solution of KOH (0.6 mL) was stirred at rt for 3 hr. The reaction mixture was acidified to pH 4 with 2N aqueous solution of HCl solution, and extracted with ethyl acetate (5 mL×3). The extracts were washed with water, dried (Na₂SO₄), and concentrated under reduced pressure. The residue was crystallized from ethanol-diethyl ether to give the desired compound (142 mg, 88%).

¹H NMR (CD₃OD, 200 MHz) δ1.47 (s, 3H), 3.31 (s, 3H), 3.38 (s, 3H), 3.51 (m, 2H), 4.34 (m, 1H), 4.65 (s, 1H), 5.04 (m, 1H), 5.73 (m, 1H), 6.56 (m, 1H), 6.73 (m, 1H), 6.91 (d, 1H), 6.97 (m, 2H), 8.04 (dd, 1H), 8.66 (m, 1H)

EXAMPLE 10

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid isopropyl ester The mixture of the indoline compound (103 mg, 0.5 mmol) obtained from preparation example 12, (2S, 3R,4R)-epoxide (141 mg, 0.5 mmol) obtained from preparation example 1, and magnesium perchlorate (112 mg, 0.5 mmol) in CH₃CN (0.3 mL) was stirred at rt for 8 hr, then concentrated under reduced pressure. The residue was purified by silica gel column chromatography (n-hexane:ethyl acetate= 4:1) to give the desired compound (198 mg, 81%), having (2S, 3R, 4S, 2'S) stereochemistry.

¹H NMR (CDCl₃, 200 MHz) δ1.27 (m, 6H) 1.57 (s, 3H), 3.37 (m, 1H), 3.48 (s, 3H), 3.49 (s, 3H), 3.58 (m, 1H), 4.02 (m, 1H), 4.13 (d, 1H), 4.44 (s, 1H0, 4.68 (m, 1H), 5.12 (d, 1H), 6.62 (m, 1H), 6.74 (m, 1H), 6.94 (d, 1H) 7.06 (m, 1H), 7.62 (m, 1H), 8.09 (dd, 1H), 8.42 (d, 1H)

EXAMPLE 11

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester The mixture of the 5-methoxyindoline compound (219 mg, 1.0 mmol) obtained from step 2 of preparation example 8, (2S, 3R, 4R)-epoxide (281 mg, 1.0 mmol) obtained from preparation example 1, and magnesium perchlorate (223 mg, 1.0 mmol) in CH₃CN (0.5 mL) was stirred at rt for 8 hr, then concentrated under reduced pressure. The residue was purified by silica gel column chromatography (n-hexane:ethyl acetate=4:1) to give the desired compound (219 mg, 45%), having (2S, 3R, 4S, 2'R) stereochemistry.

¹H NMR (CDCl₃, 200 MHz) δ1.36 (t, 3H), 1.64 (s, 3H), 3.16 (m, 1H), 3.32 (s, 3H), 3.51 (s, 3H), 3.65 (s, 3H), 3.76 (m, 1H), 4.32 (q, 2H), 4.52 (m, 1H), 4.71 (s, 1H), 4.87 (m, 1H), 5.25 (s, 1H), 5.68 (d, 1H), 6.29 (dd, 0.5H), 6.42 (dd, 0.5H), 6.66 (m, 1H), 6.82 (d, 1H), 7.60 (d, 1H), 8.02 (m, 1H), 8.33 (d, 1H)

EXAMPLE 12

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester The same procedure as the preparation of example 11 was employed to give the desired compound (225 mg, 45%), having (2S, 3R, 4S, 2'S) stereochemistry.

$^1$H NMR (CDCl$_3$, 200 MHz) δ1.31 (t, 3H), 1.57 (s, 3H), 3.29 (m, 2H), 3.39 (s, 3H), 3.48 (s, 3H), 3.67 (s, 3H), 4.32 (q, 2H), 4.62 (m, 1H), 5.12 (m, 1H), 5.42 (m, 1H), 6.37 (m, 1H), 6.71 (d, 2H), 6.93 (d, 1H), 8.05 (m, 1H), 8.90 (m, 1H)

EXAMPLE 13

Preparation of 1-[(2S, 3S, 4R)-3,4-dihydro-2-dimethixymethyl-3-hydroxy-2-methyl-6-nitro-2H-1-benzopyran-4-yl]-(2R)-2,3-dihydro-1H-5-methoxyindole-2-carboxylic acid ethyl ester The mixture of the 5-methoxyindoline compound (219 mg, 1.0 mmol) obtained from step 2 of preparation example 8, (2S, 3S, 4S)-epoxide (281 mg, 1.0 mmol) obtained from preparation example 2, and magnesium perchlorate (223 mg, 1.0 mmol) in CH$_3$CN (0.5 mL) was stirred at rt for 3 hr, then concentrated under reduced pressure. The residue was purified by silica gel column chromatography (n-hexane:ethyl acetate=4:1) to give the desired compound (214 mg, 43%), having (2S, 3S, 4R, 2'R) stereochemistry.

$^1$H NMR (CDCl$_3$, 200 MHz) δ1.22–1.55 (m, 6H), 1.64 (s, 3H), 3.16 (m, 1H), 3.32 (s, 3H), 3.51 (s, 3H), 3.65 (s, 3H), 3.76 (m, 1H), 4.32 (q, 2H), 4.52 (m, 1H), 4.71 (s, 1H), 4.87 (m, 1H), 5.25 (s, 1H), 5.68 (d, 1H), 6.35 (dd, 1H), 6.72 (m, 1H), 7.01 (m, 2H), 7.51 (d, 0.45H), 8.08 (dd, 1H), 8.87 (d, 0.55H)

EXAMPLE 14

Preparation of 1-[(2S, 3S, 4R)-3,4-dihydro-2-dimethoxymethyl-3-hydroxy-2-methyl-6-nitro-2H-1-bezopyran-4-yl]-(2S)-2,3-dihydro-1H-5-methoxyindole-2-carboxylic acid ethyl ester The same procedure as the preparation of example 13 was employed to give the desired compound (242 mg, 48%), having (2S, 3S, 4R, 2'S) stereochemistry.

$^1$H NMR (CDCl$_3$, 200 MHz) δ1.32 (m, 6H), 3.32 (m, 1H), 3.61 (s, 3H), 3.65 (s, 3H), 3.67 (s, 3H), 3.76 (m, 1H), 4.28 (q, 2H), 4.62 (m, 2H), 4.87 (m, 1H), 5.23 (s, 1H), 5.75 (d, 1H), 6.29 (dd, 1H), 6.67 (m, 2H), 7.06 (d, 1H), 7.66 (d, 0.6H), 8.01 (dd, 1H, 8.41 (d, 0.4H)

EXAMPLE 15

Preparation of 1-[(2S, 3R,4S)-3,4-dihydro-2-dimethoxymethyl-3-hydroxy-2-methyl-6-nitro-2H-1-benzopyran-4-yl]-(2R)-2,3-dihydro-1H-5-fluoroindole-2-carboxylic acid ethyl ester The mixture of the 5-fluoroindoline compound (190 mg, 0.91 mmol) obtained from preparation example 6, (2S,3R, 4R)-epoxide (256 mg, 0.91 mmol) obtained from preparation example 1, and magnesium perchlorate (223 mg, 1.0 mmol) in CH$_3$CN (0.5 mL) was stirred at rt for 8 hr, then concentrated under reduced pressure. The residue was purified by silica gel column chromatography (n-hexane:ethyl acetate=4:1) to give the desired compound (187 mg, 42%), having (2S, 3R, 4S, 2'R) stereochemistry.

$^1$H NMR (CDCl$_3$, 200 MHz) δ1.38 (t, 3H), 1.64 (s, 3H), 3.21 (m, 1H), 3.46 (s, 3H), 3.50 (s, 3H), 3.65 (m, 1H), 4.28 (q, 2H), 4.59 (d, 1H), 4.70 (s, 1H), 4.90 (m, 1H), 5.21 (s, 1H), 5.64 (m, 1H), 6.42 (m, 1H), 6.81 (m, 2H), 6.96 (d, 1H), 7.39 (d, 0.6H), 8.01 (m, 1H), 8.28 (d, 0.4H)

EXAMPLE 16

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-fluoroindole-2-carboxylic acid ethyl ester The same procedure as the preparation of example 15 was employed to give the desired compound (198 mg, 44%), having (2S, 3R, 4S, 2'S) stereochemistry.

$^1$H NMR (CDCl$_3$, 200 MHz) δ1.35 (t, 3H), 1.60 (s, 3H), 3.21 (m, 1H), 3.49 (s, 3H), 3.50 (s, 3H), 3.65 (m, 1H), 4.28 (q, 2H), 4.59 (d, 1H), 4.70 (s, 1H), 4.90 (m, 1H), 5.21 (s, 1H), 5.64 (m, 1H), 6.35 (m, 1H), 6.72 (m, 2H), 6,90 (d, 1H), 8.08 (m, 1H), 8.87 (d, 1H)

EXAMPLE 17

Preparation of 1-[(2S, 3S,4R)-3,4-dihydro-2-dimethoxymetyl-3-hydroxy-2-methyl-6-nitro-2H-1-benzopyran-4-yl]-(2R)-2,3-dihydro-1H-5-fluoroindole-2-carboxylic acid ethyl ester The mixture of the 5-fluoroindoline compound (185 mg, 0.89 mmol) obtained from preparation example 6, (2S, 3S, 4S)-epoxide (250 mg, 0.89 mmol) obtained from preparation example 2, and magnesium perchlorate (200 mg, 0.9 mmol) in CH$_3$CN (0.5 mL) was stirred at rt for 3 hr, then concentrated under reduced pressure. The residue was purified by silica gel column chromatography (n-hexane:ethyl acetate= 4:1) to give the desired compound (191 mg, 44%), having (2S, 3S, 4R, 2'R) stereochemistry.

$^1$H NMR (CDCl$_3$, 200 MHz) δ1.35 (m, 6H), 3.25 (m, 2H), 3.58 (s, 3H), 3.60 (s, 3H), 4.38 (m, 3H), 4.74 (d, 1H), 5.14 (m, 1H), 5.46 (m, 1H), 6.48 (m, 1H), 6.80 (m, 1H), 6.92 (d, 1H), 7.80 (m, 1H) 8.08 (dd, 1H), 8.85 (d, 1H)

EXAMPLE 18

1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-5-fluoroindole-2-carboxylic acid ethyl ester The same procedure as the preparation of example 17 was employed to give the desired compound (220 mg, 45%), having (2S, 3S, 4R, 2'S) stereochemistry.

$^1$H NMR (CDCl$_3$, 200 MHz) δ1.35 (t, 3H), 1.58 (s, 3H), 3.25 (m, 2H), 3.64 (s, 3H), 3.66 (s, 3H), 4.32 (q, 2H), 4.60 (s, 1H), 4.64 (d, 1H), 4.92 (m, 1H), 5.19 (s, 1H), 5.75 (m, 1H), 6.45 (m, 1H), 6.82 (m, 1H), 7.10 (dd, 1H) 7.65 (d, 0.7H), 8.02 (m, 1H) 8.22 (m, 1H), 8.34 (d, 0.3H)

EXAMPLE 19

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester The mixture of the 5-chloroindoline compound (225 mg, 1.0 mmol) obtained from preparation example 7, (2S,3R, 4R)-epoxide (281 mg, 1.0 mmol) obtained from preparation example 1, and magnesium perchlorate (223 mg, 1.0 mmol) in CH$_3$CN (0.5 mL) was stirred at rt for 8 hr, then concentrated under reduced pressure. The residue was purified by silica gel column chromatography (n-hexane:ethyl acetate 4:1) to give the desired compound (209 mg, 41%), having (2S, 3R, 4S, 2'R) stereochemistry.

$^1$H NMR (CDCl$_3$, 200 MHz) δ1.36 (t, 3H), 1.64 (s, 3H), 3.25 (m, 1H), 3.39 (s, 3H), 3.50 (s, 3H), 3.63 (m, 1H), 4.32 (q, 2H), 4.60 (m, 2H), 4.69 (s, 1H), 4.93 (m, 1H), 5.17 (s, 1H), 5.68 (d, 1H), 6.71 (m, 1H), 6.82–7.16 (m, 3H), 7.59 (d, 0.55H), 8.02 (m, 1H), 8.23 (d, 0.45H)

EXAMPLE 20

Preparation of 1-[(2S, 3R, 4S)-3,4-dihydro-2-dimethoxymethyl-3-hydroxy-2 -methyl-6-nitro-2H-1-benzopyran-4-yl]-(2S)-2,3-dihydro-1H-5-chloroindole-2-carboxylic acid ethyl ester The same procedure as the preparation of example 19 was employed to give the desired compound (203 mg, 40%), having (2S, 3R, 4S, 2'S) stereochemistry.

$^1$H NMR (CDCl$_3$, 200 MHz) δ1.34 (m, 6H), 3.30 (m, 2H), 3.64 (s, 3H), 3.65 (s, 3H), 4.32 (q, 2H), 4.60 (m, 2H), 5.14 (s, 1H), 5.74 (d, 1H), 6.71 (m, 1H), 7.07 (m, 2H), 7.67 (d, 1H), 8.04 (m, 1H), 8.24 (dd, 1H)

EXAMPLE 21

Preparation of 1-[(2S, 3R, 4R)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester The mixture of the 5-chloroindoline compound (225 mg, 1.0 mmol) obtained from preparation example 7, (2S,3S, 4S)-epoxide (281 mg, 1.0 mmol) obtained from preparation example 2, and magnesium perchlorate (223 mg, 1.0 mmol) in CH$_3$CN (0.6 mL) was stirred at rt for 3 hr, then concentrated under reduced pressure. The residue was purified by silica gel column chromatography (n-hexane:ethyl acetate= 4:1) to give the desired compound (210 mg, 41%), having 12S, 3S, 4R, 2'R) stereochemistry.

$^1$H NMR (CDCl$_3$, 200 MHz) δ1.26 (t, 3H), 1.33 (s, 3H), 3.29 (m, 2H), 3.57 (s, 3H), 3.61 (s, 3H), 4.34 (q, 2H), 4.42 (m, 1H), 4.72 (d, 1H), 5.12 (dd, 1H), 5.50 (d, 1H), 6.73 (dd, 1H), 7.20 (m, 3H) 8.09 (d, 1H), 8.36 (d, 0.3H) 8.82 (d, 0.7H)

EXAMPLE 22

Preparation of 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester The same procedure as the preparation of example 21 was employed to give the desired compound (220 mg, 45%), having (2S, 3S, 4R, 2'S) stereochemistry.

$^1$H NMR (CDCl$_3$, 200 MHz) δ1.34 (m, 6H), 3.30 (m, 2H), 3.64 (s, 3H), 3.65 (s, 3H), 4.32 (q, 2H), 4.60 (m, 2H), 5.14 (s, 1H), 5.74 (d, 1H), 6.71 (m, 1H), 7.07 (m, 2H), 7.67 (d, 0.6H), 8.04 (m, 1H), 8.24 (dd, 1H), 8.32 (d, 0.4H)

EXAMPLE 23

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid methyl ester The mixture of the 5-chloroindoline compound (212 mg, 1.0 mmol) obtained from preparation example 10, (2S,3R, 4R)-epoxide (281 mg, 1.0 mmol) obtained from preparation example 1, and magnesium perchlorate (223 mg, 1.0 mmol) in CH$_3$CN (0.6 mL) was stirred at rt for 8 hr, then concentrated under reduced pressure. The residue was purified by silica gel column chromatography (n-hexane:ethyl acetate= 4:1) to give the desired compound (218 mg, 44%), having (2S, 3R, 4S, 2'R) stereochemistry.

$^1$H NMR (CDCl$_3$, 200 MHz) δ1.64 (s, 3H), 3.25 (m, 1H), 3.39 (s, 3H), 3.50 (s, 3H), 3.69 (m, 1H), 3.88 (s, 3H), 4.27 (m, 1H0, 4.43 (s, 1H0, 4.64 (d, 1H), 4.95 (d, 1H), 5.68 (m, 1H), 6.44 (dd, 1H), 6.72 (m, 1H), 6.94 (m, 1H), 7.07 (m, 1H), 7.60 (d, 0.5H), 8.06 (m, 1H), 8.22 (d, 0.55H)

EXAMPLE 24

1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid methyl ester The same procedure as the preparation of example 23 was employed to give the desired compound (196 mg, 40%), having (2S, 3R, 4S, 2'S) stereochemistry.

$^1$H NMR (CDCl$_3$, 200 MHz) δ1.56 (s, 3H), 3.38 (m, 2H), 3.48 (s, 6H), 3.88 (s, 3H), 4.21 (m, 1H), 4.63 (m, 1H), 5.14 (m, 1H), 5.42 (m, 1H), 6.71 (m, 1H), 6.92 (d, 1H), 7.04 (m, 2H), 8.08 (dd, 1H), 8.89 (m, 1H)

EXAMPLE 25

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl amide To the solution of the compound (130 mg, 0.26 mmol) obtained from example 23 in methanol (0.5 mL), 70% aqueous solution of ethyl amide (0.5 mL) was added. The reaction mixture was stirred at rt for 8 hr and extracted with ethyl acetate (10 ml×3) . The extracts were dried (Na$_2$SO$_4$), filtered, and concentrated under reduced pressure. The residue was purified by silica gel column chromatography (n-hexane:ethyl acetate=3:2) to give the desired compound (119 mg, 92%)

$^1$H NMR (CDCl$_3$, 200 MHz) δ1.26 (t, 3H) 1.68 (s, 3H), 3.28 (m, 2H), 3.37 (s, 3H), 3.45 (s, 3H), 3.68 (q, 2H), 4.34 (m, 1H), 4.49 (s, 1H), 4.59 (d, 1H), 4.79 (m, 1H), 5.77 (d, 1H), 6.68 (d, 1H), 6.91 (d, 1H), 7.03 (s, 1H), 7.65 (d, 1H), 7.99 (m, 2H)

EXAMPLE 26

1-[(2S, 3R, 4S)-3,4-dihydro-2 -dimethoxymethyl-3-hydroxy-2-methyl-6-nitro-2H-1-benzopyran-4-yl]-(2S)-2,3-dihydro-1H-5-chloroindole-2-carboxylic acid ethyl amide The reaction was proceeded by the same method used for the preparation of example 25, except using the compound (130 mg, 0.26 mmol) obtained from example 18 as a starting material. The residue was purified by silica gel column chromatography (n-hexane:ethyl acetate=3:2) to give the desired compound (122 mg, 94%)

$^1$H NMR (CDCl$_3$, 200 MHz) δ1.26 (t, 3H), 1.57 (s, 3H), 3.18 (m, 2H), 3.39 (s, 3H), 3.54 (s, 3H), 3.63 (q, 2H), 3.83 (dd, 1H), 4.05 (d, 1H), 4.46 (s, 1H), 5.04 (d, 1H), 6.67 (d, 1H), 6.89 (d, 1H), 7.16 (s, 1H), 7.59 (m, 1H), 7.74 (d, 1H), 8.06 (dd, 1H)

EXAMPLE 27

Preparation of 1-[(2S, 3R, 4S)-3,4-dihydro-2-dimethoxymethyl-3-hydroxy-2-methyl-6-nitro-2H-1-benzopyran-4-yl]-(2R)-2,3-dihydro-5-chloro-1H-2-hydroxymethylindole The mixture of the indoline compound (184 mg, 1.0 mmol) obtained from step 2 of preparation example 11, (2S, 3R, 4R)-epoxide (281 mg, 1.0 mmol) obtained from preparation example 1, and magnesium perchlorate (223 mg, 1.0 mmol) in $CH_3CN$ (0.6 mL) was stirred at rt for 8hr, then concentrated under reduced pressure. The residue was purified by silica gel column chromatography (n-hexane:ethyl acetate=1:1) to give the desired compound (207 mg, 45%), having (2S, 3R, 4S, 2'R) stereochemistry.

$^1H$ NMR ($CDCl_3$, 200 MHz) $\delta$1.64 (s, 3H), 3.28 (m, 2H), 3.36 (s, 3H), 3.51 (s, 3H), 3.65 (d, 1H), 3.97 (m, 1H), 4.28 (m, 2H), 4.47 (M, 1H), 4.74 (d, 1H), 5.40 (d, 1H), 6.62 (dd, 1H), 6.94 (s, 1H), 6.99 (m, 2H), 7.73 (d, 1H), 8.06 (dd, 1H)

EXAMPLE 28

Preparation of 1-[(2S, 3R, 4S)-3,4-dihydro-2-dimethoxymethyl-3-hydroxy-2-methyl-6-nitro-2H-1-benzopyran-4-yl]-(2S)-2,3-dihydro-5-chloro-1H-2-hydroxymethylindole The same procedure as the preparation of example 27 was employed to give the desired compound (142 mg, 31%), having (2S, 3R, 4S, 2'S) stereochemistry.

$^1H$ NMR ($CDCl_3$, 200 MHz) $\delta$1.55 (s, H), 3.34 (m, 1H), 3.40 (s, 3H), 3.50 (s, 3H), 3.62 (m, 1H), 3.94 (m, 2H), 4.34 (m, 1H), 4.42 (m, 1H), 4.89 (m, 1H), 5.42 (m, 1H), 6.62 (m, 1H), 6.94 (m, 3H), 8.03 (m, 1H), 8.42 (m, 1H)

EXAMPLE 29

Preparation of 1-[(2R, 3S, 4 R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester The mixture of the indoline compound (191 mg, 1.0 mmol) obtained from preparation example 5, (2R, 3S,4S)-epoxide (281 mg, 1.0 mmol) obtained from preparation example 3, and magnesium perchlorate (223 mg, 1.0 mmol) in $CH_3CN$ (0.6 mL) was stirred at rt for 8hr, then concentrated under reduced pressure. The residue was purified by silica gel column chromatography (n-hexane ethyl acetate= 4:1) to give the desired compound (218 mg, 46%), having (2R, 3S, 4R, 2'S) stereochemistry.

$^1H$ NMR ($CDCl_3$, 200 MHz) $\delta$1.32 (t, 3H), 1.60 (s, 3H), 3.16 (m, 1H), 3.28 (s, 3H), 3.47 (s, 3H), 3.62 (m, 1H), 4.32 (q, 2H), 4.56 (m, 1H), 4.88 (m, 1H), 5.21 (s, 1H), 5.74 (d, 1H), 6.54 (dd, 1H), 6.70 (m, 1H), 6.91 (m, 1H), 7.08 (m, 2H), 7.58 (d, 0.6H), 7.95 (dd, 1H), 8.24 (d, 0.4H)

EXAMPLE 30

Preparation of 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester The same procedure as the preparation of example 29 was employed to give the desired compound (195 mg, 41%), having (2R, 3S, 4R, 2'R) stereochemistry.

$^1H$ NMR ($CDCl_3$, 200 MHz) $\delta$1.36 (m, 3H), 1.56 (s, 3H), 3.36 (m, 2H), 3.46 (s, 3H), 3.56 (s, 3H), 4.34 (q, 2H), 4.62 (d, 1H), 5.15 (dd, 1H), 5.60 (d, 1H), 6.62 (dd, 1H), 6.74 (m, 1H), 6.84 (d, 1H), 7.08 (m, 2H), 7.8 (d, 0.4H), 8.08 (dd, 1H), 8.9 (d, 0.6H)

EXAMPLE 31

Preparation of 1-[(2R, 3R,4S)-3,4-dihydro-2-dimethoxymethyl-3-hydroxy-2-methyl-6-nitro-2H-1-benzopyran-4-yl]-(2S)-2,3-dihydro-1H -indole-2-carboxylic acid ethyl ester The mixture of the indoline compound (191 mg, 1.0 mmol) obtained from preparation example 5, (2R, 3R, 4R)-epoxide (281 mg, 1.0 mmol) obtained from preparation example 4, and magnesium perchlorate (223 mg, 1.0 mmol) in $CH_3CN$ (0.6 mL) was stirred at rt for 3 hr, then concentrated under reduced pressure. The residue was purified by silica gel column chromatography (n-hexane:ethyl acetate= 4:1) to give the desired compound (211 mg, 45%), having (2R, 3R, 4S, 2'S) stereochemistry.

$^1H$ NMR ($CDCl_3$, 200 MHz) $\delta$1.35 (m, 6H), 3.28 (m, 2H), 3.55 (s, 3H), 3.62 (s, 3H), 4.35 (q, 2H), 4.80 (m, 1H), 5.16 (m, 1H), 5.61 (d, 1H), 6.62 (dd, 1H), 6.80 (m, 1H), 6.94 (d, 1H), 7.10 (m, 2H), 7.82 (d, 0.6H), 8.08 (m, 1H), 8.90 (d, 0.4H)

EXAMPLE 32

1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester The same procedure as the preparation of example 31 was employed to give the desired compound (202 mg, 43%), having (2R, 3R, 4S, 2'R) stereochemistry.

$^1H$ NMR ($CDCl_3$, 200 MHz) $\delta$1.35 (m, 6H), 3.38 (m, 2H), 3.64 (s, 3H), 3.66 (s, 3H), 4.29 (q, 2H), 4.68 (m, 1H), 4.9 (m, 1H), 5.22 (s, 1H), 5.88 (d, 1H), 6.61 (m, 1H), 6.72 (m, 1H), 6.84 (dd, 1H), 7.07 (m, 2H), 7.68 (d, 0.6H), 8.02 (m, 1H), 8.34 (d, 0.4H)

EXAMPLE 33

Preparation of 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid n-propyl ester The mixture of indoline-2-carboxylic acid n-propyl ester (205 mg, 1.0 mmol), (2R, 3S, 4S)-epoxide (281 mg, 1.0 mmol) obtained from preparation example 3, and magnesium perchlorate (223 mg, 1.0 mmol) in $CH_3CN$ (0.6 mL) was stirred at rt for 3 hr, then concentrated under reduced pressure. The residue was purified by silica gel column chromatography (n-hexane:ethyl acetate=4:1) to give the desired compound (168 mg, 35% ), having (2R, 3S, 4R, 2'S) stereochemistry.

$^1H$ NMR ($CDCl_3$, 200 MHz) $\delta$1.32 (t, 3H), 1.60 (s, 3H), 1.73 (q, 2H), 3.22 (m, 1H), 3.41 (s, 3H), 3.52 (s, 3H), 3.66 (m, 1H), 4.32 (m, 2H), 4.59 (d, 1H), 4.72 (s, 1H), 4.93 (m, 1H), 5.29 (s, 1H), 5.79 (d, 1H), 6.59 (dd, 1H), 6.75 (dd, 1H), 6.86 (m, 1H), 7.09 (m, 2H), 7.62 (d, 0.6H), 8.01 (m, 1H), 8.28 (d, 0.4H)

EXAMPLE 34

Preparation of 1[-(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid n-propyl ester The same procedure as the preparation of example 33 was employed to give the desired compound (188 mg, 39%), having (2R, 3R, 4S, 2'R) stereochemistry.

¹H NMR (CDCl₃, 200 MHz) δ0.94 (t, 3H), 1.58 (m, 6H), 1.73 (q, 2H), 3.29 (m, 2H), 3.46 (s, 3H), 3.48 (s, 3H), 4.22 (m, 2H), 4.44 (m, 1H), 4.71 (m, 1H), 5.19 (s, 1H), 5.58 (d, 1H), 6.58–6.80 (m, 3H), 6.93 (d, 1H), 7.08 (m, 1H), 8.06 (m, 1H), 8.79 (d, 1H)

EXAMPLE 35

1-[(2R, 3S, 4R)-3,4-dihydro-2-dimethoxymethyl-3-hydroxy-2-methyl-6-nitro-2H-1-benzopyran-4-yl]-(2S)-2, 3-dihydro-1H-5-methoxyindole-2-carboxylic acid ethyl ester The mixture of the 5-methoxyindoline compound (219 mg, 1.0 mmol) obtained from preparation example 8, (2R, 3S, 4S) epoxide (281 mg, 1.0 mmol) obtained from preparation example 3, and magnesium perchlorate (223 mg, 1.0 mmol) in CH₃CN (0.6 mL) was stirred at rt for 8 hr, then concentrated under reduced pressure. The residue was purified by silica gel column chromatography (n-hexane:ethyl acetate=4:1) to give the desired compound (219 mg, 44%), having (2R, 3S, 4R, 2'S) stereochemistry.

¹H NMR (CDCl₃, 200 MHz) δ1.36 (t, 3H), 1.64 (s, 3H), 3.16 (m, 1H), 3.32 (s, 3H), 3.51 (s, 3H), 3.65 (s, 3H), 3.76 (m, 1H), 4.32 (q, 2H), 4.52 (m, 1H), 4.71 (s, 1H), 4.87 (m, 1H), 5.25 (s, 1H), 5.68 (d, 1H), 6.29 (dd, 0.5H), 6.42 (dd, 0.5H), 6.66 (m, 1H), 6.82 (d, 1H), 7.60 (d, 1H), 8.02 (m, 1H), 8.33 (d, 1H)

EXAMPLE 36

Preparation of 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester The same procedure as the preparation of example 35 was employed to give the desired compound (201 mg, 40%), having (2R, 3S, 4R, 2'R) stereochemistry.

¹H NMR (CDCl₃, 200 MHz) δ1.31 (t, 3H), 1.57 (s, 3H), 3.29 (m, 2H), 3.39 (s, 3H), 3.48 (s, 3H), 3.67 (s, 3H), 4.32 (q, 2H), 4.62 (m, 1H), 5.12 (m, 1H), 5.42 (m, 1H), 6.37 (m, 1H), 6.71 (d, 2H), 6.93 (d, 1H), 8.05 (m, 1H), 8.90 (m, 1H)

EXAMPLE 37

Preparation of 1-[(2R, 3R, 4S)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester The mixture of the 5-methoxyindoline compound (219 mg, 1.0 mmol) obtained from preparation example 8, (2R, 3R, 4R)-epoxide (281 mg, 1.0 mmol) obtained from preparation example 4, and magnesium perchlorate (223 mg, 1.0 mmol) in CH₃CN (0.6 mL) was stirred at rt for 3 hr, then concentrated under reduced pressure. The residue was purified by silica gel column chromatography (n-hexane:ethyl acetate=4:1) to give the desired compound (222 mg, 44%), having (2R, 3R, 4S, 2'S) stereochemistry.

¹H NMR (CDCl₃, 200 MHz) δ1.25–1.55 (m, 6H), 1.64 (s, 3H), 3.16 (m, 1H), 3.32 (s, 3H), 3.51 (s, 3H), 3.65 (s, 3H), 3.76 (m, 1H), 4.32 (q, 2H), 4.52 (m, 1H), 4.71 (s, 1H), 4.87 (m, 1H), 5.25 (s, 1H), 5.68 (d, 1H), 6.35 (dd, 1H), 6.72 (m, 1H), 7.01 (m, 2H), 7.51 (d, 0.45H) 8.08 (dd, 1H), 8.87 (d, 0.55H)

EXAMPLE 38

Preparation of 1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester The same procedure as the preparation of example 37 was employed to give the desired compound (211 mg, 42%), having (2R, 3R, 4S, 2'R) stereochemistry.

¹H NMR (CDCl₃, 200 MHz) δ1.32 (m, 6H), 3.32 (m, 1H), 3.61 (s, 3H), 3.65 (s, 3H), 3.67 (s, 3H), 3.76 (m, 1H), 4.28 (q, 2H), 4.62 (m, 2H), 4.87 (m, 1H), 5.23 (s, 1H), 5.75 (d, 1H), 6.29 (dd, 1H), 6.67 (m, 2H), 7.06 (d, 1H), 7.66 (d, 0.6H), 8.01 (dd, 1H, 8.41 (d, 0.4H)

EXAMPLE 39

Preparation of 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl amide The reaction was proceeded by the same method used for the preparation of example 25, except using the compound (70 mg, 0.26 mmol) obtained from example 35 as a starting material. The residue was purified by silica gel column chromatography (n-hexane:ethyl acetate=3:2) to give the desired compound (53 mg, 76%).

¹H NMR (CDCl₃, 200 MHz) δ1.22 (t, 1H), 1.68 (s, 3H), 3.21 (m, 2H), 3.36 (s, 3H), 3.46 (s, 3H), 3.67 (s, 3H), 3.72 (q, 2H), 4.32 (m, 1H), 4.45 (s, 1H), 4.52 (m, 1H), 4.68 (m, 1H), 5.83 (d, 1H), 6.34 (m, 1H), 6.70 (s, 1H), 6.91 (d, 1H), 7.68 (m, 1H), 7.96 (dd, 1H), 8.13 (m, 1H)

EXAMPLE 40

Preparation of 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester The mixture of the 5-chloroindoline compound (225 mg, 1.0 mmol) obtained from preparation example 7, (2R, 3S, 4S)-epoxide (281 mg, 1.0 mmol) obtained from preparation example 3, and magnesium perchlorate (223 mg, 1.0 mmol) in CH₃CN (0.6 mL) was stirred at rt for 8 hr, then concentrated under reduced pressure. The residue was purified by silica gel column chromatography (n-hexane:ethyl acetate=4:1) to give the desired compound (224 mg, 44%), having (2R, 3S, 4R, 2S) stereochemistry.

¹H NMR (CDCl₃, 200 MHz) δ1.36 (t, 3H), 1.64 (s, 3H), 3.25 (m, 1H), 3.39 (s, 3H), 3.50 (s, 3H), 3.63 (m, 1H), 4.32 (q, 2H), 4.60 (m, 2H), 4.69 (s, 1H), 4.93 (m, 1H), 5.17 (s, 1H), 5.68 (d, 1H), 6.71 (m, 1H), 6.82–7.16 (m, 3H), 7.59 (d, 0.55H), 8.02 (m, 1H), 8.23 (d, 0.45H)

EXAMPLE 41

Preparation of 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester The same procedure as the preparation of example 40 was employed to give the desired compound (191 mg, 38%), having (2R, 3S, 4R, 2'R) stereochemistry.

¹H NMR (CDCl₃, 200 MHz) δ1.34 (m, 6H), 3.30 (m, 2H), 3.64 (s, 3H), 3.65 (s, 3H), 4.32 (q, 2H), 4.60 (m, 2H), 5.14 (s, 1H), 5.74 (d, 1H), 6.71 (m, 1H), 7.07 (m, 2H), 7.67 (d, 1H), 8.04 (m, 1H), 8.24 (dd, 1H)

EXAMPLE 42

Preparation of 1-[(2S, 3R, 4S)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester To a solution of the compound prepared from (200 mg, 0.42 mmol) example 1 in methanol (5 mL) was added (0.5 mL, 0.2 mmol, 0.5 eq) 0.4M of aqueous Cu(OAc)$_2$ solution, with stirring, followed by sodium borohydride (160 mg, 4.2 mmol, 10 eq) slowly for 30 min. The reaction mixture was stirred for 1 hr at rt, extracted with ethyl acetate (10 mL) and filtered to remove a precipitated black solid. The filtrate was washed with the saturated aqueous NaHCO$_3$ solution (10 mL), then the aqueous layer was extracted with ethyl acetate (30 mL). The combined organic layer was washed with brine, dried (Na$_2$SO$_4$), filtered and concentrated under reduced pressure. The residue was purified by silica gel chromatography (n-hexane:ethyl acetate=2:1) to give the desired compound (161 mg, 85%).

$^1$H NMR (CDCl$_3$, 200 MHz) δ1.25 (t, 3H), 1.55 (s, 3H), 3.05 (1H, m), 3.40 (d, 1H), 3.46 (s, 3H), 3.51 (s, 3H), 4.22 (q, 2H), 4.52–4.75 (m, 3H), 6.45–6.78 (m, 5H), 7.02–7.20 (2H, m)

EXAMPLE 43

1-[(2S, 3R, 4S)-6-amino-3,4-dihydro-2-dimethoxymethyl-3-hydroxy-2-methyl-2H-1-benzopyran-4-yl]-(2S)-2,3-dihydro-1H-indole-2carboxylic acid ethyl ester The reaction was proceeded by the same method used for the preparation of example 42, except using the compound prepared from example 2 (200 mg, 0.42 mmol) as a starting material. The residue was purified by silica gel chromatography (n-hexane:ethyl acetate 2:1) to give the desired compound (146 mg, 76%).

$^1$H NMR (CDCl$_3$, 200 MHz) δ1.30 (t, 3H), 1.48 (s, 3H), 3.20 (m, 2H), 3.45 (s, 3H), 3.48 (s, 3H), 4.32 (q, 2H), 4.52 (m, 1H), 5.18 (m, 1H), 5.72 (m, 1H), 6.48–6.82 (m, 5H), 7.02 (d, 2H)

EXAMPLE 44

Preparation of 1-[(2S, 3S, 4R)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester The reaction was proceeded by the same methode used for the preparation of example 42, except using the compound prepared from example 3 (200 mg, 0.42 mmol) as a starting material. The residue was purified by silica gel chromatography (n-hexane:ethyl acetate=2:1) to give the desired compound (135 mg, 72%).

$^1$H NMR (CDCl$_3$, 200 MHz) δ1.26 (s, 3H), 1.34 (t, 3H), 3.18 (m, 1H), 3.51 (s, 3H), 3.61 (s, 3H), 3.92 (m, 1H), 4.28 (q, 2H), 4.58 (m, 1H), 5.18 (d, 1H), 5.29 (s, 1H), 5.76 (d, 1H), 6.21 (d, 1H), 6.45–6.80 (m, 4H), 7.08 (m, 2H)

EXAMPLE 45

Preparation of 1-[(2S, 3S, 4R)-6-amino-3,4-dihydro-2-dimethoxymethyl-3-hydroxy-2-methyl-2H-1-benzopyran-4-yl]-(2S)-2,3-dihydro-1H-indole-2-carboxylic acid ethyl ester The reaction was proceeded by the same method used for the preparation of example 42, except using the compound prepared from example 4 (200 mg, 0.42 mmol) as a starting material. The residue was purified by silica gel chromatography (n-hexane:ethyl acetate=2:1) to give the desired compound (142 mg, 76%).

$^1$H NMR (CDCl$_3$, 200 MHz) δ1.26 (s, 3H), 1.32 (t, 3H), 3.38 (m, 2H), 3.62 (s, 3H), 3.64 (s, 3H), 4.16 (m, 1H), 4.35 (q, 2H), 4.56 (s, 1H), 4.65 (m, 1H), 4.92 (m, 1H), 6.04 (d, 1H), 6.46 (dd, 1H), 6.50–6.84 (m, 3H) 7.09 (m, 2H)

EXAMPLE 46

Preparation of 1-[(2S, 3R, 4S)-3,4-dihydro-2-dimethoxymethyl-3-hydroxy-2-methyl-6-nitro-2H-1-benzopyran-4-yl]-1H-indole- 2-carboxylic acid ethyl ester To the solution of the compound (200 mg, 0.42 mmol) prepared from example 1 or 2 in benzene (10 mL) was added DDQ (170 mg, 0.76 mmol, 1.8 eq) . The reaction mixture was stirred at rt for 5 hr, and diluted with ethyl acetate (10 mL) . The solution was washed with 10% aqueous NaOH solution (10 mL) and water (10 mL), dried (Na$_2$SO$_4$), filtered, and concentrated under reduced pressure. The residue was purified by silica gel chromatography (n-hexane:ethyl acetate=2:1) to give the desired compound (167 mg, 85%).

$^1$H NMR (CDCl$_3$, 200 MHz) δ1.44 (t, 3H), 1.62 (s, 3H), 3.47 (d, 2H), 3.52 (s, 3H), 3.55 (s, 3H), 4.38 (d, 1H), 4.41 (q, 2H), 4.61 (s, 1H), 6.46 (d, 1H), 6.98–7.12 (m, 3H), 7.25 (d, 1H), 7.45 (s, 1H), 7.68 (m, 1H), 8.12 (dd, 1H)

EXAMPLE 47

Preparation of 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid ethyl ester The reaction was proceeded by the same method used for the preparation of example 46, except using the compound prepared from example 3 or 4 (200 mg, 0.42 mmol) as a starting material. The residue was purified by silica gel chromatography (n-hexane:ethyl acetate=2:1) to give the desired compound (143 mg, 72%).

$^1$H NMR (CDCl$_3$, 200 MHz) δ1.45 (t, 3H), 1.47 (s, 3H), 3.36 (d, 2H), 3.59 (s, 3H), 3.60 (s, 3H), 4.40 (q, 2H), 4.46 (s, 1H), 4.75 (dd, 1H), 6.55 (d, 1H), 7.07 (m, 3H), 7.45 (s, 1H), 7.73 (m, 2H), 8.10 (dd, 1H)

EXAMPLE 48

Preparation of 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid methyl ester The reaction was proceeded by the same method used for the preparation of example 46, except using the compound prepared from example 5 or 6 (300 mg, 0.65 mmol) as a starting material. The residue was purified by silica gel chromatography (n-hexane:ethyl acetate=2:1) to give the desired compound (284 mg, 95%).

$^1$H NMR (CDCl$_3$, 200 MHz) δ1.63 (s, 3H), 3.48 (d, 1H), 3.54 (s, 3H), 3.56 (s, 3H), 3.96 (s, 3H), 4.36 (m, 1H), 4.62 (s, 1H), 6.47 (d, 1H), 7.06 (m, 2H), 7.33 (d, 1H), 7.46 (s, 1H), 7.70 (m, 2H), 8.11 (dd, 1H)

EXAMPLE 49

Preparation of 1-[(2S, 3s, 4R)-3,4-dihydro-2-dimethoxymethyl-3-hydroxy-2 -methyl-6-nitro-2H-1-benzopyran-4-yl]-1H-indole-2-carboxylic acid methyl ester The reaction was proceeded by the same method used for the preparation of example 46, except using the compound prepared from example 7 or 8 (300 mg, 0.65 mmol) as a starting material. The residue was purified by silica gel chromatography (n-hexane:ethyl acetate=2:1) to give the desired compound (290 mg, 96%).

$^1$H NMR (CDCl$_3$, 200 MHz) δ1.49 (s, 3H), 3.36 (d, 1H), 3.60 (s, 3H), 3.62 (s, 3H), 3.98 (s, 3H), 4.48 (s, 1H), 4.76 (dd, 1H), 6.59 (d, 1H), 7.08 (m, 3H), 7.45 (s, 1H), 7.72 (m, 2H), 8.11 (dd, 1H)

EXAMPLE 50

Preparation of 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid The reaction was proceeded by the same procedure used for the preparation of example 9, except using the compound prepared from example 48 (137 mg, 0.3 mmol) as a starting material. The residue was recrystallized from ethanol/diethyl ether to give the desired compound (120 mg, 91%).

$^1$H NMR (CD$_3$OD, 200 MHz) δ1.42 (s, 3H), 3.53 (s, 3H), 3.58 (d, 1H), 3.64 (s, 3H), 4.57 (s, 1H), 6.57 (dd, 1H), 7.01–7.22 (m, 4H), 7.56 (d, 1H), 7.66 (m, 1H), 8.11 (dd, 1H)

EXAMPLE 51

Preparation of 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid The reaction was proceeded by the same method used for the preparation of example 9, except using the compound prepared from example 49 (137 mg, 0.3 mmol) as a starting material. The residue was recrystallized from ethanol/diethyl ether to give the desired compound (115 mg, 91%).

$^1$H NMR (CD$_3$OD, 200 MHz) δ1.54 (s, 3H), 3.53 (s, 3H), 3.55 (s, 3H), 3.55 (d, 1H), 4.36 (d, 1H), 4.76 (s, 1H), 6.53 (dd, 1H), 6.8–7.1 (m, 3H), 7.32 (s, 1H), 7.48 (d, 1H) 7.66 (dd, 1H), 8.06 (dd, 1H)

EXAMPLE 52

Preparation of 1-[(2S, 3R, 4S)-6-amino-3,4-dihydro-2-dimethoxymethyl-3-hydroxy-2-methyl-2H-1-benzopyran-4-yl]-1H-indole-2-carboxylic acid ethyl ester The reaction was proceeded by the same method used for the preparation of example 42, except using the compound prepared from example 46 (150 mg, 0.32 mmol) as a starting material. The residue was purified by silica gel chromatography (n-hexane:ethyl acetate=2:1) to give the desired compound (112 mg, 80%).

$^1$H NMR (CDCl$_3$, 200 MHz) δ1.44 (t, 3H), 1.52 (s, 3H), 3.42 (d, 1H), 3.54 (s, 3H), 3.58 (s, 3H), 4.25 (d, 1H), 4.38 (q, 2H), 4.66 (s, 1H), 6.19 (d, 1H), 6.58 (dd, 1H), 6.74 (m, 1H), 6.80 (d, 1H), 7.05 (m, 2H), 7.41 (s, 1H), 7.64 (m, 1H)

EXAMPLE 53

Preparation of 1-[(2S, 3S, 4R)-6-amino-3,4-dihydro-2-dimethoxymethyl-3-hydroxy-2-methyl-2H-1-benzopyran-4-yl]-1H-indole-2-carboxylic acid ethyl ester The reaction was proceeded by the same procedure used for the preparation of example 42, except using the compound prepared from example 47 (140 mg, 0.30 mmol) as a starting material. The residue was purified by silica gel chromatography (n-hexane:ethyl acetate=2:1) to give the desired compound (99 mg, 76%).

$^1$H NMR (CDCl$_3$, 200 MHz) δ1.40 (s, 3H), 1.44 (t, 3H), 3.44 (m, 1H), 3.56 (s, 3H), 3.60 (s, 3H), 4.12 (d, 1H), 4.50 (q, 2H), 4.65 (d, 1H), 6.17 (d, 1H), 6.56 (dd, 1H), 6.80 (m, 2H), 7.08 (m, 2H), 7.39 (s, 1H), 7.69 (m, 1H)

EXAMPLE 54

Preparation of 1-[(2S, 3R, 4S)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester The mixture of the quinoline compound (191 mg, 1.0 mmol) prepared from preparation example 13, (2S, 3R,4R)-epoxide (281 mg, 1.0 mmol) prepared from preparation example 1, and magnesium perchlorate (223 mg, 1.0 mmol) in CH$_3$CN (0.6 mL) was stirred at rt for 8 hr, then concentrated under reduced pressure. The residue was purified by silica gel column chromatography (n-hexane:ethyl acetate=4:1) to give the desired compound (162, 35%), having (2S 3R 4S 2'R) stereochemistry.

$^1$H NMR (CDCl$_3$, 200 MHz) δ1.56 (s, 3H), 2.18 (m, 1H), 2.42 (m, 1H), 2.72 (dd, 1H), 2.93 (dd, 1H), 3.49 (s, 3H), 3.50 (s, 3H), 3.75 (s, 3H), 3.82 (m, 1H), 4.57 (d, 1H), 4.78 (s, 1H), 5.79 (d, 1H), 6.76 (m, 1H), 6.92 (d, 1H), 7.05 (d, 1H), 7.12 (m, 2H), 8.00 (s, 1H), 8.05 (m, 1H)

EXAMPLE 55

Preparation of 1-[(2S, 3R, 4S)- 3,4-dihydro-2-dimethoxymethyl-3-hydroxy-2-methyl-6-nitro-2H-1-benzopyran-4-yl]-(2S)-1,2,3, 4-tetrahydro-1H-quinoline-2-carboxylic acid methyl ester The same procedure as the preparation of example 54 was employed to give the desired compound (177 mg, 38%), having (2S, 3R, 4S, 2'S) stereochemistry.

$^1$H NMR (CDCl$_3$, 200 MHz) δ1.57 (s, 3H), 2.15 (m, 2H), 2.78 (m, 2H), 3.40 (s, 3H), 3.47 (s, 3H), 3.82 (s, 3H), 3.92 (m, 1H), 4.62 (s, 1H), 5.25 (d, 1H), 5.92 (d, 1H), 6.6–7.2 (m, 5H), 8.15 (m, 2H)

EXAMPLE 56

Preparation of 1-[(2S, 3S, 4R)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester The mixture of the quinoline compound (191 mg, 1.0 mmol) prepared from preparation example 13, (2S, 3S, 4S)-epoxide (281 mg, 1.0 mmol) prepared from preparation example 2, and magnesium perchlorate (223 mg, 1.0 mmol) in CH$_3$CN (0.6 mL) was stirred at rt for 3 hr, then concentrated under reduced pressure. The residue was purified by silica gel column chromatography (n-hexane:ethyl acetate=4:1) to give the desired compound (175, 37%), having (2S, 3S, 4R, 2'R) stereochemistry.

$^1$H NMR (CDCl$_3$, 200 MHz) δ1.49 (s, 3H), 2. 12 (m, 1H), 2.20 (m, 1H), 2.72 (dd, 1H), 2.88 (dd, 1H), 3.60 (s, 3H), 3.64 (s, 3H), 3.72 (s, 3H), 3.92 (m, 1H), 4.33 (d, 1H), 4.60 (s, 1H), 5.39 (d, 1H), 6.78 (m, 1H), 7.04–7.18 (m, 4H), 8.05 (m, 2H)

EXAMPLE 57

Preparation of 1-[(2S, 3S, 4R)-3,4-dihydro-2-dimethoxymethyl-3-hydroxy-2-methyl-6-nitro-2H-1-benzopyran-4-yl]-(2S)-1,2,3,4-tetrahydro-1H-quinoline-2-carboxylic acid methyl ester The same procedure as the preparation of example 56 was employed to give the desired compound (170 mg, 36%) having (2S, 3S, 4R, 2'S) stereochemistry.

¹H NMR (CDCl₃, 200 MHz) δ1.58 (s, 3H), 2.30 (m, 2H), 2.8 (m, 2H), 3.63 (, 3H), 3.64 (s, 3H), 3.83 (s, 3H), 4.28 (m, 1H), 4.61 (s, 1H), 5.03 (d, 1H), 6.00 (d, 1H), 6.61 (m, 1H), 6. 2 (dd, 1H), 6.85 (d, 1 H),6.95 (m, 1H), 7.90 (m, 1H), 8.05 (m, 2H)

EXAMPLE 58

Preparation of (2S, 2aR, 4aR,10aS)-[(3,4-b)-2a,10a-dihydro-2-dimethoxymehyl-2-methyl- 12-nitro-2H-1-benzopyrano]-[(1,2-d)-4a,5-dihydro-10H-indolino]-4-oxomorpholine To the precooled solution of the compound prepared from example 5 (92 mg, 0.2 mmol) in CH₂Cl₃ at −20° C., was added diisopropylamine (22 mg, 0.23 mmol, 1.11 eq) and 1.8 M of diethyl aluminum chloride in toluene (0.11 mL, 0.2 mmol, 1.0 eq.). The reaction mixture was stirred at −20° C. for 2 hr, then at rt for 4 hr, and poured over precooled saturated aqueous solution of Na₂CO₃ (15 mL) The mixture was extracted with ethyl acetate (10 mL×3), and the organic layer was dried (Na₂SO₄), filtered and concentrated under reduced pressure. The residue was purified by silica gel column chromatography (n-hexane:ethyl acetate=4:1) to give the desired compound (72 mg, 85%).

¹H NMR (CDCl₃, 200 MHz) δ1.54 (s, 3H), 3.37 (s, 3H), 3.41 (m, 1H), 3.48 (s, 3H), 3.54 (m, 1H), 4.58 (dd, 1H), 4.67 (m, 1H), 5.14 (d, 1H), 5.81 (m, 1H), 6.62 (d, 1H), 6.82 (m, 2H), 7.05 (d, 1H), 7.17 (m, 1H), 8.13 (dd, 1H), 8.46 (d, 1H)

EXAMPLE 59

Preparation of (2S, 2aR, 4aS, 10aS)-[(3,4-b)-2a, 10a-dihydro-2-dimethoxymethyl-2-methyl-12-nitro-2H-1-benzopyrano]-[(1,2-d)-4a,5 -dihydro-10H-indolino]-4-oxomorpholine The reaction was proceeded by the same method used for the preparation of example 58, except using the compound prepared from example 6 (92 mg, 0.20 mmol) as a starting material. The residue was purified by silica gel chromatography (n-hexane:ethyl acetate=2:1) to give the desired compound (69 mg, 81%).

¹H NMR (CDCl₃, 200 MHz) δ1.66 (s, 3H), 3.24 (m, 1H), 3.38 (s, 3H), 3.48 (m, 1H), 3.54 (s, 3H), 3.82 (d, 1H), 4.55 (d, 1H), 4.57 (s, 1H), 4.79 (d, 1H), 6.61 (d, 1H), 6.94 (m, 2H), 7.23 (m, 2H), 8.09 (m, 2H)

EXAMPLE 60

Preparation of (2S, 2aS, 4aR,10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine The reaction was proceeded by the same method used for the preparation of example 58, except using the compound prepared from example 7 (92 mg, 0.20 mmol) as a starting material. The residue was purified by silica gel chromatography (n-hexane:ethyl acetate 2:1) to give the desired compound (68 mg, 81%).

¹H NMR (CDCl₃, 200 MHz) δ1.56 (s, 3H), 3.41 (m, 1H), 3.51 (s, 3H), 3.60 (s, 3H), 3.88 (d, 1H), 4.23 (d, 1H), 4.48 (s, 1H), 4.61 (d, 1H), 4.87 (d, 1H), 6.60 (d, 1H), 6.88–7.30 (m, 4H), 8.18 (m, 2H)

EXAMPLE 61

Preparation of (2S, 2aS, 4aS,10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine The reaction was proceeded by the same method used for the preparation of example 58, except using the compound prepared from example 8 (135 mg, 0.30 mmol) as a starting material. The residue was purified by silica gel chromatography (n-hexane:ethyl acetate=2:1) to give the desired compound (106 mg, 86%).

¹H NMR (CDCl₃, 200 MHz) δ1.43 (s, 3H), 3.46 (s, 3H), 3.49 (d, 1H), 3.59 (m, 1H), 3.62 (s, 3H), 4.47 (s, 1H), 4.68 (dd, 1H), 4.81 (d, 1H), 5.19 (d, 1H), 5.81 (m, 1H), 6.83 (m, 2H), 7.19 (m, 3H), 8.2 (dd, 1H), 8.52 (d, 1H)

EXAMPLE 62

Preparation of (2S, 2aR, 10aS)-[(3,4-b)-2a,10a-dihydro-2-dimethoxymethyl-2-methyl-12-nitro-2H-1-benzopyrano]-[(1,2-d)-10H-indolino]-4-oxomorpholine To the cooled solution of the compound (120 mg, 0.27 mmol) prepared from example 50 in tetrahydrofuran (6 mL) at 0° C. was added diisopropyl amine (65 μL, 0.36 mmol) and methyl chloroformate (25 μL, 0.3 mmol). The reaction mixture was stirred for 6 hr with slowly increasing the temperature to rt, then was concentrated under reduced pressure. The residue was purified by silica gel chromatography (n-hexane:ethyl acetate=2:1) to give the desired compound (11 mg, 2.6%).

¹H NMR (CDCl₃, 200 MHz) δ1.59 (s, 3H), 3.52 (s, 3H), 3.59 (m, 1H), 3.53 (s, 3H), 4.14 (d, 2H), 4.28 (d, 1H), 4.57 (s, 1H), 6.83 (m, 1H), 7.19 (m, 3H), 7.65 (s, 1H), 7,72 (m, 2H), 8.15 (dd, 1H)

EXAMPLE 63

Preparation of (2S, 2aS, 10aR)-[(3,4-b)-2a,10a-dihydro-2-dimethoxymethyl-2-methyl-12-nitro-2H-1-benzopyrano]-[(1,2-d)-10H-indolino]-4-oxomorpholine To the cooled solution of the compound (130 mg, 0.29 mmol) prepared from example 51 in tetrahydrofuran (6 mL) at 0° C. was added diisopropyl amine (65 μL, 0.36 mmol) and idobutyl chloroformate (45 μL, 0.32 mmol). The reaction mixture was stirred for 6 hr with slowly increasing the temperature to rt, then was concentrated under reduced pressure. The residue was purified by silica gel chromatography (n-hexane:ethyl acetate=2:1) to give the desired compound (3 mg, 7.3%).

¹H NMR (CDCl₁, 200 MHz) δ1.56 (s, 3H), 3.46 (s, 3H), 3.57 (s, 3H), 4.48 (s, 1H), 4.93 (d, 1H), 5.42 (d, 1H), 7.04 (m, 1H), 7.21 (d, 1H), 7.38 (m, 1H), 7.42 (m, 1H), 7.72 (s, 1H), 7.82 (d, 1H), 8.18 (m, 2H)

The compounds prepared in the above examples were listed in Table 1a and 1b.

TABLE 1

| Example | $R_1$ | $R_2$ | $R_3$ | $R_4$ | n |  | stereochemistry |
|---|---|---|---|---|---|---|---|
| 1 | $NO_2$ | 6 | OH | $CO_2CH_2CH_3$ | H |  | 0 | 2S, 3R, 4S, 2'R |
| 2 | $NO_2$ | 6 | OH | $CO_2CH_2CH_3$ | H |  | 0 | 2S, 3R, 4S, 2'S |
| 3 | $NO_2$ | 6 | OH | $CO_2CH_2CH_3$ | H |  | 0 | 2S, 3S, 4R, 2'R |
| 4 | $NO_2$ | 6 | OH | $CO_2CH_2CH_3$ | H |  | 0 | 2S, 3S, 4R, 2'S |
| 5 | $NO_2$ | 6 | OH | $CO_2CH_3$ | H |  | 0 | 2S, 3R, 4S, 2'R |
| 6 | $NO_2$ | 6 | OH | $CO_2CH_3$ | H |  | 0 | 2S, 3R, 4S, 2'S |
| 7 | $NO_2$ | 6 | OH | $CO_2CH_3$ | H |  | 0 | 2S, 3S, 4R, 2'R |
| 8 | $NO_2$ | 6 | OH | $CO_2CH_3$ | H |  | 0 | 2S, 3S, 4R, 2'S |
| 9 | $NO_2$ | 6 | OH | $CO_2H$ | H |  | 0 | 2S, 3R, 4S, 2'S |
| 10 | $NO_2$ | 6 | OH | $CO_2CH(CH_3)_2$ | H |  | 0 | 2S, 3R, 4S, 2'S |
| 11 | $NO_2$ | 6 | OH | $CO_2CH_2CH_3$ | $OCH_3$ | 5' | 0 | 2S, 3R, 4S, 2'R |
| 12 | $NO_2$ | 6 | OH | $CO_2CH_2CH_3$ | $OCH_3$ | 5' | 0 | 2S, 3R, 4S, 2'S |
| 13 | $NO_2$ | 6 | OH | $CO_2CH_2CH_3$ | $OCH_3$ | 5' | 0 | 2S, 3S, 4R, 2'R |
| 14 | $NO_2$ | 6 | OH | $CO_2CH_2CH_3$ | $OCH_3$ | 5' | 0 | 2S, 3S, 4R, 2'S |
| 15 | $NO_2$ | 6 | OH | $CO_2CH_2CH_3$ | F | 5' | 0 | 2S, 3R, 4S, 2'R |
| 16 | $NO_2$ | 6 | OH | $CO_2CH_2CH_3$ | F | 5' | 0 | 2S, 3R, 4S, 2'S |
| 17 | $NO_2$ | 6 | OH | $CO_2CH_2CH_3$ | F | 5' | 0 | 2S, 3S, 4R, 2'R |
| 18 | $NO_2$ | 6 | OH | $CO_2CH_2CH_3$ | F | 5' | 0 | 2S, 3S, 4R, 2'S |
| 19 | $NO_2$ | 6 | OH | $CO_2CH_2CH_3$ | Cl | 5' | 0 | 2S, 3R, 4S, 2'R |
| 20 | $NO_2$ | 6 | OH | $CO_2CH_2CH_3$ | Cl | 5' | 0 | 2S, 3R, 4S, 2'S |
| 21 | $NO_2$ | 6 | OH | $CO_2CH_2CH_3$ | Cl | 5' | 0 | 2S, 3S, 4R, 2'R |
| 22 | $NO_2$ | 6 | OH | $CO_2CH_2CH_3$ | Cl | 5' | 0 | 2S, 3S, 4R, 2'S |
| 23 | $NO_2$ | 6 | OH | $CO_2CH_3$ | Cl | 5' | 0 | 2S, 3R, 4S, 2'R |
| 24 | $NO_2$ | 6 | OH | $CO_2CH_3$ | Cl | 5' | 0 | 2S, 3R, 4S, 2'S |
| 25 | $NO_2$ | 6 | OH | $CONHCH_2CH_3$ | Cl | 5' | 0 | 2S, 3R, 4S, 2'R |
| 26 | $NO_2$ | 6 | OH | $CONHCH_2CH_3$ | Cl | 5' | 0 | 2S, 3R, 4S, 2'S |
| 27 | $NO_2$ | 6 | OH | $CH_2OH$ | Cl | 5' | 0 | 2S, 3R, 4S, 2'R |
| 28 | $NO_2$ | 6 | OH | $CH_2OH$ | Cl | 5' | 0 | 2S, 3R, 4S, 2'S |
| 29 | $NO_2$ | 6 | OH | $CO_2CH_2CH_3$ | H |  | 0 | 2R, 3R, 4S, 2'S |
| 30 | $NO_2$ | 6 | OH | $CO_2CH_2CH_3$ | H |  | 0 | 2R, 3S, 4R, 2'R |
| 31 | $NO_2$ | 6 | OH | $CO_2CH_2CH_3$ | H |  | 0 | 2R, 3R, 4S, 2'S |
| 32 | $NO_2$ | 6 | OH | $CO_2CH_2CH_3$ | H |  | 0 | 2R, 3R, 4S, 2'R |
| 33 | $NO_2$ | 6 | OH | $CO_2CH_2CH_3$ | H |  | 0 | 2R, 3S, 4R, 2'S |
| 34 | $NO_2$ | 6 | OH | $CO_2CH_2CH_3$ | H |  | 0 | 2R, 3R, 4R, 2'R |
| 35 | $NO_2$ | 6 | OH | $CO_2CH_2CH_3$ | $OCH_3$ | 5 | 0 | 2R, 3R, 4R, 2'S |
| 36 | $NO_2$ | 6 | OH | $CO_2CH_2CH_3$ | $OCH_3$ | 5 | 0 | 2R, 3S, 4R, 2'R |
| 37 | $NO_2$ | 6 | OH | $CO_2CH_2CH_3$ | $OCH_3$ | 5 | 0 | 2R, 3R, 4S, 2'S |
| 38 | $NO_2$ | 6 | OH | $CO_2CH_2CH_3$ | $OCH_3$ | 5 | 0 | 2R, 3R, 4S, 2'R |
| 39 | $NO_2$ | 6 | OH | $CO_2NHCH_2CH_3$ | $OCH_3$ | 5 | 0 | 2R, 3S, 4R, 2'S |
| 40 | $NO_2$ | 6 | OH | $CO_2CH_2CH_3$ | Cl | 5 | 0 | 2R, 3S, 4R, 2'S |
| 41 | $NO_2$ | 6 | OH | $CO_2CH_2CH_3$ | Cl | 5 | 0 | 2R, 3R, 4R, 2'R |
| 42 | $NH_2$ | 6 | OH | $CO_2CH_2CH_3$ | H |  | 0 | 2S, 3R, 4S, 2'R |
| 43 | $NH_2$ | 6 | OH | $CO_2CH_2CH_3$ | H |  | 0 | 2S, 3R, 4S, 2'S |
| 44 | $NH_2$ | 6 | OH | $CO_2CH_2CH_3$ | H |  | 0 | 2S, 3S, 4R, 2'R |
| 45 | $NH_2$ | 6 | OH | $CO_2CH_2CH_3$ | H |  | 0 | 2S, 3S, 4R, 2'S |
| 46* | $NO_2$ | 6 | OH | $CO_2CH_2CH_3$ | H |  | 0 | 2S, 3R, 4S |
| 47* | $NO_2$ | 6 | OH | $CO_2CH_2CH_3$ | H |  | 0 | 2S, 3S, 4R |
| 48* | $NO_2$ | 6 | OH | $CO_2CH_3$ | H |  | 0 | 2S, 3R, 4S |
| 49* | $NO_2$ | 6 | OH | $CO_2CH_3$ | H |  | 0 | 2S, 3S, 4R |
| 50* | $NO_2$ | 6 | OH | $CO_2H$ | H |  | 0 | 2S, 3R, 4S |
| 51* | $NO_2$ | 6 | OH | $CO_2H$ | H |  | 0 | 2S, 3S, 4R |
| 52* | $NH_2$ | 6 | OH | $CO_2CH_2CH_3$ | H |  | 0 | 2S, 3R, 4S |
| 53* | $NH_2$ | 6 | OH | $CO_2CH_2CH_3$ | H |  | 0 | 2S, 3S, 4R |
| 54 | $NO_2$ | 6 | OH | $CO_2CH_3$ | H |  | 1 | 2S, 3R, 4S, 2'S |
| 55 | $NO_2$ | 6 | OH | $CO_2CH_3$ | H |  | 1 | 2S, 3R, 4S, 2'R |
| 56 | $NO_2$ | 6 | OH | $CO_2CH_3$ | H |  | 1 | 2S, 3S, 4R, 2'S |
| 57 | $NO_2$ | 6 | OH | $CO_2CH_3$ | H |  | 1 | 2S, 3R, 4S, 2'R |
| 58 | $NO_2$ | 6 |  |  | H |  | 0 | 2S, 3R, 4S, 2'R |
| 59 | $NO_2$ | 6 |  |  | H |  | 0 | 2S, 3R, 4S, 2'S |
| 60 | $NO_2$ | 6 |  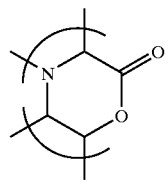  | | H |  | 0 | 2S, 3S, 4R, 2'R |
| 61 | $NO_2$ | 6 |  |  | H |  | 0 | 2S, 3S, 4R, 2'S |
| 62* | $NO_2$ | 6 |  |  | H |  | 0 | 2S, 3R, 4S |
| 63* | $NO_2$ | 6 |  |  | H |  | 0 | 2S, 3S, 4R |

46–53, 62, 63 compounds have 2'-3' double bond of heterocycle.

Formulation examples

The pharmaceutical composition containing the compound of formula 1 as an active ingredient can be administered orally or parenterally. The method for preparation of an injection solution for parenteral administration and the method for preparation of syrup and a tablet for oral administration are illustrated as the followings.

Formulation Example 1

Preparation of an Injection Solution

The injection solution containing 10 mg of the compound of formula 1 as an active ingredient was prepared as the followings.

The compound of example 1, NaCl and 0.1 g of ascorbic acid were dissolved in distilled water to make 100 mL of solution. The solution was filled in a bottle and sterilized by heating for 30 min at 20° C.

An injection solution of the present invention consists of the followings:

The compound of example 1 . . . 1 g
NaCl . . . 0.6 g
Ascorbic acid . . . 1 g
Distilled water . . . q.s

Formulation Example 2

Preparation of Syrup

The syrup containing 2% of the compound of formula 1 as an active ingredient was prepared as the followings.

The compound of formula 1, saccharine, and saccharide were dissolved in 80 g of warm water. After the solution was cooled, glycerine, saccharine, flavor, ethanol, and sorbic acid were added. The distilled water was added to the mixture to make 100 mL of solution.

Syrup composition of the present invention consists of the followings:

The compound of example 1 . . . 2 g
Saccharine . . . 0.8 g
Saccharide 25.4 g
Glycerine . . . 8.0 g
Flavor . . . 0.04 g
Ethanol . . . 4.0 g
Sorbic acid . . . 0.4 g
Distilled water . . . q.s

Formulation Example 3

Preparation of an Tablet

The tablet containing 15 mg of the compound of formula 1 as an active ingredient was prepared as the followings.

250 g of the compound of example 1 was mixed with 175.9 g of lactose, 180 g of starch and 32 g of colloidal silicic acid, and then 10% of gelatin solution was added. The resultant mixture was ground and passed through a 14-mesh sieve and then dried. 160 g of starch, 50 g of talc and 5 g of magnesium stearate were added and blended. The resultant mixture was made into the tablet by conventional method.

A tablet of the present invention consists of the followings:

The compound of example 1 . . . 250 g
Lactose . . . 175.9 g
Starch . . . 340 g
Colloidal silicic acid . . . 32 g
10% of gelatin solution . . . 340 g
talc . . . 50 g
Magnesium stearate . . . 5 g

Experimental Examples

The following experiments were made on the compounds of the chemical formula 1 to investigate their pharmacological properties.

Experimental Example 1

Vasodilation Effects on Isolated Aorta of Rats

The following experiment was conducted to examine whether the compounds of the chemical formula 1 have the vasodilating effect.

Male Sprague-Dawly rats (350–450 g, obtained from the Experimental Animal Team of the Korea Research Institute of Chemical Technology) were knocked unconscious by hitting the occipital region, sacrificed by cervical dislocation, and underwent thoracotomy. After being quickly removed, the thoracic aorta was deprived of the adipose tissue and cut into aortic rings of 3 mm width. The aorta was lightly rubbed with cotton club soaked in a modified Krebs Henseleit buffer (Physiological Salt Solution, PSS) to remove the inner epithelial layer therefrom. While being hung in an organ bath containing a physiological buffer, the vascular smooth muscle was allowed to equilibrate under a resting tension of 2 g and then, stand for 1 hour at 37° C. for stabilization, supplying a carbogen consisting of 95% $O_2$-5% $CO_2$.

Thereafter, the vascular smooth muscle was constricted with $10^{-5}$ M phenylephrine and washed several times with PSS and this procedure was repeated again to ensure the stable reacivity of vascular smooth muscle to repetitive constriction/relaxation.

Thereafter, $3\times10^{-6}$ M methoxamine was applied to induce an intensive constriction in the vascular smooth muscle. When the vasoconstriction induced by the methoxamine was reached and maintained to a maximum, test compounds and controls were cumulatively added to the organ baths in concentrations of 1, 3, 10 and 30 $\mu$M so as to examine the vasodilation effect. Cromakalim and BMS-180448, both known to be the first generation $K_{ATP}$ opener with potent vasodilatation and cardioprotection effects, were used as the controls.

The change rate of constriction by the addition of the drugs compared to the maximal constriction induced by methoxamine was calculated to plot a concentration-relaxation response curve. Through a linear regression analysis, $IC_{50}$, the drug concentration at which the vascular tissue is 50% relaxed to the maximal constricton, was obtained for each drug. The results are given in Table 2, below.

TABLE 2

Vasodilatation Effect of Compounds of Chemical Formula 1

| Test Drugs | Vasodilation ($IC_{50}$, $\mu$M) |
| --- | --- |
| CromaKalim | 0.067 |
| BMS-180448 | 1.38 |

TABLE 2-continued

Vasodilatation Effect of Compounds of Chemical Formula 1

| Test Drugs | Vasodilation (IC$_{50}$, μM) |
|---|---|
| EX. 2 | 24.3 |
| EX. 6 | 15.6 |
| EX. 11 | 16.5 |
| EX. 15 | >30 |
| EX. 20 | >30 |
| EX. 30 | >30 |
| EX. 35 | >30 |
| EX. 36 | >30 |
| EX. 48 | 24 |
| EX. 56 | 11.4 |
| EX. 62 | >30 |

Cromakalim represented a potent vasodilating effect having 0.067 μM of IC$_{50}$ on the isolated rat aorta constricted with methoxamine (3 μM) while IC$_{50}$ of BMS-180448 was 1.38 μM, showing a twenty times weaker vasodilation effect than that of Cromakalim. On the other hand, the compounds of the present invention ranged, in IC$_{50}$, from 11.4 μM to greater than 30 μM, so that their vasodilatation effects were significantly weaker than those of the controls, Cromakalim and BMS-180448.

When exerting their actions on the K$_{ATP}$ present in the heart, the compounds according to the present invention play a role in protecting the heart. On the other hand, the K$_{ATP}$ openers acting on the K$_{ATP}$ present in peripheral vascular smooth muscle dilate the blood vessels, lowering the blood pressure. Hypotension may mask any cardioprotective effects due to reduction in coronary artery perfusion pressure, and would limit utility in treating myocardial ischemia. Therefore, the compounds of the present invention may be more optimal for cardioprotectives by virtue of their weak vasodilatation activity.

As illustrated above, the compounds of the present invention are so low in the vasorelaxant potencies that they are improved in the selectivity for heart protective function.

Experiment Example 2

Cardioprotective Activity in Isolated Ischemic Heart Models of Rats

In order to determine whether the compounds of the chemical formula 1 are protective for ischemic hearts in vitro, experiments determining the anti-ischemic effects of the compounds on isolated rat hearts were conducted as follows.

For all in vitro studies, isolated rat hearts were used according to the published methods after some modification [H J Ring, *Arzneim.-Forsch./Drug Res.* 39 (II), 1535 (1989): T. Krzeminski, et al., *J. Pharmacological Methods*, 25, 95, (1991)].

Male Sprague-Dawley rats weighing 300–450 g were anesthetized with sodium pentobarbital (100 mg/kg, i.p.). The tail vein was injected with heparin (1,000 U/kg) and then the trachea was intubated. While rats were mechanically ventilated with a rodent ventilator (Model 7025, Ugobasile, Italy), their hearts were perfused in situ with oxygenated modified Krebs-Henseleit bicarbonate buffer (described herein) by retrograde aortic cannulation. The hearts were then excised and moved to a Langendorff apparatus (H.S.E., Germany), where they were perfused with oxygenated modified Krebs-Henseleit bicarbonate buffer containing (in mM) NaCl 116, NaHCO$_3$ 24.9, KCl 4.7, MgSO$_4$ 1.1, KH$_2$PO$_4$ 1.17, CaCl$_2$ 2.52, glucose 8.32 and pyruvate 2.0 at a constant perfusion pressure (85 mm Hg). A latex balloon filled with solvent (ethanol: water=1:1 (v/v)) and attached to a metal cannula was placed in the left ventricle through pulmonary vein and connected to a Isotec pressure transducer (H.S.E., Germany) for measurement of left ventricular pressure (LVP). The hearts were allowed to equilibrate for 15 min, at which time left ventricular end-diastolic pressure (EDP) was adjusted to 5 mm Hg and this balloon volume was maintained throughout the experiment. Then, baseline contractile function, heart rate (HR), and coronary flow (CF) (extracorporeal electromagnetic flow probe, Narco Bio-System, U.S.A.) were measured. Cardiac contractile function was calculated by subtracting LVEDP from LV peak systolic pressure (LVSP), yielding developed pressure (LVDP). Double product (DP), another important parameter for assessing cardiac performance, was calculated by multiplying HR by LVDP. Throughout the experiment, all these parameters were measured, and calculated before and 10 min after pretreatment with each compound and 30 min after the onset of reperfusion with buffer. Data on reperfusion DP were further expressed as the percentage to pretreatment DP.

After stabilization for 15 min, the hearts were pretreated for 10 min with respective drugs (10 μM, 0.04% DMSO) or vehicle (0.04% DMSO) before onset of global ischemia; test agents were administered directly into the oxygenator of the Langendorff apparatus immediately above the aortic root in a retrograde fashion as solutions in the perfusate. We then rendered the hearts globally ischemic by completely shutting off the perfusate for 30 min. Severity of ischemia was determined as the time to contracture (TTC, min) during global ischemia in which the first 5 mmHg increase in EDP was observed. Then, the hearts were reperfused and, 30 min later, contractile function (LVDP, DP) and cumulative reperfusion lactate dehydrogenase (LDH) release were measured. LDH was measured as a sensitive index for loss of cell viability with a kit supplied by Boerhinger Mannheim based on the technique of Wroblewski and LaDue [F. Wroblewski and JS. La Due, *Proc Soc Exp Biol Med* 90, 210, (1955)].

TABLE 3

Cardioprotective Effect of Compounds of Chemical Formula 1

| | Cardioprotection on Ischemic heart (10 μM) | | | |
|---|---|---|---|---|
| Test Drugs | LDVP × HR (%) | EDP (MmHg) | TTC (min) | LDH (U/g) |
| Vehicle | 23.0 | 43.4 | 20.3 | 29.9 |
| BMS-180448 | 67.6 | 16.5 | 27.8 | 17.2 |
| EX. 2 | 55.1 | 25.7 | 22.6 | 17.8 |
| EX. 6 | 62.2 | 21 | 24.5 | 10.4 |
| EX. 11 | 66.5 | 14.7 | 22.9 | 13.3 |
| EX. 15 | 53.3 | 2.7 | 24.8 | 12.0 |
| EX. 30 | 64.1 | 11.3 | 27.1 | 9.2 |
| EX. 35 | 57.3 | 19 | 25.1 | 23.2 |
| EX. 36 | 53.1 | 23.3 | 24.7 | 18.9 |
| EX. 48 | 79.5 | 9.5 | 22.0 | 16.7 |
| EX. 56 | 61.0 | 29.0 | 22.2 | 18.8 |
| EX. 62 | 67.2 | 36.5 | 23.1 | 20.5 |

In vehicle-treated group, reperfusion DP (LVDP×HR), a index for contractility function, was decreased to 23.0% of pretreatment DP, and EDP was increased to 43.3 mmHg from 5 mmHg, and TTC was 20.3 min, and reperfusion LDH release was 29.9 U/g as shown in the above table 3. In BMS-190448 treated group, reperfusion contractile function (DP, LVDP×HR) was 67.6% of pretreatment DP, which was significantly improved compared to vehicle treated group. EDP was 16.5 mmHg, significantly lower than control, and TTC was 27.8 min, prolonged than control, and reperfusion LDH release was 17.2 U/g, decreaed than control. Then, in BMS-180448 treated group all parameters showed significant protective effect on ischemic heart. When compared only in anti-ischemic effect from those parameters, LVDP× HR, EDP, TTC, and LDH release, the compounds of the present invention were similar to or superior to BMS-180448. However, because the compounds of the present invention are remarkably lower vasorelaxant effect than BMS-180448 does, they are far superior to the conventional drug in cardioselective antiischemic activity. Especially, the compound of example 30 showed a good cardioprotective effect, of which contractile function (LVDP×HR) was improved to 64.1% of pretreatment index, and EDP was 11.3 mmHg, and TTC was 27.1 min, and reperfusion LDH release was 9.2 U/g, with very low vasodilation activity (>30 $\mu$M). So, it shows much better cardioselectivity upon vasodilation than is BMS-180448. Consequently, the compounds of the present invention can be used for the treatment of ischemic heat diseases by virtue of their excellent selectivity and protective activity against ischemic cardiovascular diseases. In addition, the compounds of the present invention is useful in the protection or treatment for organs or diseases related to "ischemia-reperfusion" injury such as brain, neuronal cells, retina, or organ besides heart.

Experiment Example 3

Cardioprotective Activity in Ischemic Heart Models of Rats

In order to determine whether the compounds of the chemical formula 1 are protective for ischemic hearts, experiments determining the anti-ischemic effects of the compounds on rats were conducted as follows.

Male rats (350–450 g, obtained from the Experimental Animal Team of the Korea Research Institute of Chemical Technology) were anesthetized by the intraperitoneal injection of pentobarbital at a dose of 75 mg/kg. After trachetomy, the rats were rendered to respire artificially at a rate of 60/min with a stroke volume of 10 ml/kg. Cannulars were inserted into the fermoral vein and the fermoral artery and used for drug administration and blood pressure measurement, respectively.

In the ischemic myocardial injury models, the body temperature has an important influence on the results. To avoid the change in the body temperature, a body temperature measuring probe was inserted into the rectum of each rat and the body temperature was constantly kept at 37° C. with the aid of a homeothermic blanket control unit.

Afterwards, during testing, a continuous measurement was made of the mean arterial blood pressures and heart rates from the rats. For the measurement of the blood pressure, a pressure transducer, such as that manufactured by Grass Ins., MA, U.S.A., identified as Model Statham P23XL, was used.

The heart rate was measured by a tachometer, such as that manufactured by Gould Inc., Ohio, U.S.A., identified as Biotachometer. In addition, all of the changes occurring were continuously recorded through the Gould 2000 chart recorder, manufactured by Gould Inc.

The left coronary artery was occluded according to the Selye H. method as follows. The rats underwent a left thoracotomy operation for partial opening of the chest and the right-side chest was pressurized by the middle finger of the left hand to push the heart out. Immediately after the left anterior descending coronary artery hereinafter referred to as (LAD) was carefully stitched using a suture needle with 5-0 silk ligature, the heart was then repositioned in the thoracic cavity while both ends of the ligature were situated outside. The opposite ligature ends were passed through a PE tube (PE100, 2.5 cm) and allowed to stand loose for 20 min for stabilization. Via the cannula inserted into the femoral vein, vehicles or drugs were administered into the rats which were rendered to stand for 30 min in order to sufficiently elicit the efficacies of the drugs. BMS-180448 was used as a control drug and the i.v.administration dose was 0.3 mg/kg for all test drugs of interest and the control drug.

Next, the PE tube which had the doubled strands of the ligature passed therethrough was pushed toward the heart and then, set upright by tightly pulling end regions of the ligature with a hemostatic pincette while pressing the coronary artery. The PE tube was allowed to stand for 45 min for the occlusion of the coronary artery, followed by the removal of the hemostatic pincette and then, by the reperfusion for 90 min.

After the reocclusion of the coronary artery in accordance with the above procedure, the rats were administered with 2 ml of a 1% Evans blue through an intravenous route. Subsequently, an excess of pentobarbital was intravenously injected to kill the rats, after which the heat was removed and then, deprived of the right ventricle and both atria. The left ventricle was cut horizontally to the heart apex into 5 or 6 slices which were weighed. From the surface of each slice, images were input with the aid of a Hi-scope into a computer installed with an image analyzing program (Image Pro Plus). From the images input into the computer, the area of the normal blood stream tissue region which appeared blue in a computer monitor and the area which appeared colorless were measured. The percentage of the colorless area to the total area of each slice was calculated and multiplied by the weight of each slice to determine the area at risk (AAR) of each slice. The AAR obtained from each slice was summed for all slices and the total AAR was divided by the total weight of the left ventricle to yield % AAR, as shown in the following mathematical formula 1:

$AAR(\%)$=(summed AAR for all slices)/(total weight of left ventricle)×100  [Mathematical Formula 1]

In addition, the heart slices were incubated for 15 min in 2,3,5-triphenyltetrazolium chloride (TTC) phosphate buffer (pH 7.4) at 37° C. and fixed for 20–24 hours in a 10% formalin solution. During this fixation, 2,3,5-triphenyltetrazolium chloride was reduced into formazan dye by the myocardial dehydrogenase and its cofactor NADH, so that the normal regions of the tissue were colored brick-red. In contrast, the infarct zones of the tissue were deficient in the dehydrogenase and its cofactor, so that no reduction occurred on the 2,3,5-triphenyltetrazolium, allowing the color to remain unchanged.

According to whether the tissue regions were colored by 2,3,5-triphenyltetrazolium, a measurement was made of the areas of the normal and infarct zones in each ventricle slice. The infarct zone area of each slice was summed for all slices and the resulting summed infarct zone area was divided by total AAR weight or total left ventricle weight to yield % IZ as shown in the following mathematical formula 2:

$IZ(\%)$=(summed infarct zone area)/(total left ventricle area)×100  [Mathematical Formula 2]

TABLE 4

Anti-Ischemic Effect of Compounds of Chemical Formula 1

| Test Drug | Anti-ischemic effect Rat in vivo (0.3 mg/kg) | |
| --- | --- | --- |
| | AAR/LV (%) | IZ/AAR (%) |
| Vehicle | 39.8 | 60.8 |
| BMS-180448 | 38.8 | 39.1 |
| EX. 2 | 32.6 | 39.1 |
| EX. 11 | 38.3 | 42.1 |
| EX. 20 | 35.4 | 35.1 |
| EX. 30 | 33.6 | 38.9 |
| EX. 35 | 31.6 | 37.8 |
| EX. 36 | 37.5 | 41.4 |

In the ischemic myocardium damage model of anesthetized rats, as seen in Table 4, the vehicle-treated group showed a myocardial infarction rate to area at risk (IZ/AAR) of 60.8%, which indicates a serious damage in the myocardial muscle. Being measured to be 39.1% in myocardial infarction rate, BMS-180448 showed noticeable anti-ischemic activity. When compared only in myocardial infarction rate, the compounds of the present invention were similar to or superior to BMS-180448. However, because the compounds of the present invention are remarkably lower in vasodilatation activity than is BMS-180448, they are superior to the conventional drug in cardioselective anti-ischemic activity. Especially, the compound of Example 20, 30 and 35 were of very low vasodilatation activity ($IC_{50}>30\ \mu M$) with a myocardial infarction rate of as low as 35.1%, 38.9%, and 37.8%, respectively, so it shows much better cardioselectivity upon vasodilatation than is BMS-180448. Further, the compounds of the present invention did not act to reduce the blood pressure. Consequently, the compounds of the present invention can be used as a curative for the treatment of ischemic heart diseases by virtue of their excellent protective activity against ischemic cardiovascular diseases.

Experimental Example 4

Protective Activity for Neuronal Cells

In order to examine whether the compounds of the chemical formula 1 suppress the iron-induced damage and death of neuronal cells, experiments were conducted as follows.

From the brains of 17–18 day-old rat embryos, cerebral cortical neurons were isolated and then, cultured at 37° C. for 7–9 days in a 5% $CO_2$ incubator. The cortical cell cultures were washed twice with a minimum essential medium (MEM) to reduce the serum concentration to 0.2% and pre-treated for 30 min with 30 $\mu M$ of each of test compounds. For the experiments, the test compounds were dissolved in DMSO and diluted in a medium. At this time, the final concentration of DMSO was not allowed to exceed 0.2%. For a control group, only vehicle was applied.

After the pre-treatment with test compounds or vehicle, $FeSO_4$ was added to a final concentration of 50 uM, and the cultures were maintained for 24 hours in a $CO_2$ incubator. During incubation, lactate dehydrogenase (LDH) was released into the medium upon neuronal death by the oxidative toxicity of iron. The extent of neuronal damage was assessed by measuring the amount of LDH released into the media. The protective effect of the compounds of interest on neurons was evaluated by calculating the LDH reduction rate of treatment group compared with that of the control group. The results are given in Table 5, below.

TABLE 5

Protective Effect of Compounds of Chemical Formula 1 on Neurons

| Compound | Concentration of compound ($\mu M$) | % Protection |
| --- | --- | --- |
| EX. 2 | 30 | 79 |
| EX. 4 | 30 | 98 |
| EX. 5 | 30 | 79 |
| EX. 12 | 30 | 85 |
| EX. 16 | 30 | 73 |
| EX. 20 | 30 | 69 |
| EX. 42 | 30 | 100 |
| EX. 43 | 30 | 101 |
| EX. 44 | 30 | 89 |
| EX. 45 | 30 | 96 |
| EX. 52 | 30 | 100 |
| EX. 53 | 30 | 94 |
| EX. 54 | 30 | 101 |
| EX. 63 | 30 | 100 |

As seen in Table 5, the compounds of the present invention protected neurons from being damaged by iron. The compounds of Example 42, 43, 52, 54, and 63 protected the neuronal death completely by as high as 100% at 30 $\mu M$. In addition, the compound of Example 4, 45, and 53 showed higher than 90% of protection rate, which demonstrates that the compounds have very potent protective activity against the iron-included damage to neurons.

Since the compounds of the present invention showed an excellent protective effects on neurons, they can be used as preventive or curative agents for the medical treatment of the neurological disorders caused by the damage or death of neurons, such as cerebral stroke and dementia as well as for the medical treatment of inflammatory diseases such as arthritis, cardiac infarction, and acute/chronic tissue damage.

Experimental Example 5

Inhibitory Activity Against Lipid Peroxidation

In order to examine whether the compounds of the chemical formula 1 suppress the iron-induced lipid peroxidation, experiments were conducted as follows.

The rat brain was homogenized in a Krebs buffer (15 mM HEPES, 10 mM glucose, 140 mM NaCl, 3.6 mM KCl, 1.5 mM $CaCl_2$, 1.4 mM $KH_2PO_4$, 0.7 mM $MgCl_2$, pH 7.4) and the supernatant separated by centrifugation at 12,000 rpm for 10 min was used for further experiments. $FeCl_2$ was added to a final concentration of 400 $\mu M$ in the brain homogenate which was then allowed to stand at 37° C. for 30 min for the facilitation of oxidation. Each of the test compounds was added at a concentration of 100 $\mu M$ and vehicle was used as a control.

Iron facilitates the oxidation of the brain homogenate to produce malondialdehyde (MDA), a lipid peroxidation product. Thus, the lipid peroxidation was determined by MDA quantification. The inhibitory effect of the test compounds against the lipid peroxidation was evaluated by calculating MDA reduction rate of the test compounds compared with that of the control group.

Typically, the MDA quantification is achieved by reacting samples with 2-thiobarbituric acid (TBA) and measuring the absorbance at 530 nm. However, this method is unsuitable to treat samples on a large scale because of a boiling step. Thus, in this experiment, N-methyl-2-phenylindole was used instead of TBA. In this case, one molecule of MDA reacts with two molecules of N-methyl-2-phenylindole to form a chromogen which shows a maximal absorbance at 586 nm and requires no boiling steps. Bioxytech$^R$ LPO-586 Kit was used for MDA quantification. The results are given in Table 6, below.

TABLE 6

Inhibitory Effect of Compounds of Chemical Formula 1 on Lipid Peroxidation

| Compounds | Concentration of drugs ($\mu$M) | % Inhibition |
|---|---|---|
| EX. 42 | 100 | 90 |
| EX. 43 | 100 | 93 |
| EX. 44 | 100 | 90 |
| EX. 45 | 100 | 81 |
| EX. 52 | 100 | 95 |
| EX. 53 | 100 | 91 |

As seen in Table 6, the compounds of the present invention suppress the iron-induced lipid peroxidation. In particular, the compounds of Examples 42, 43, 44, 52, and 53 showed very potent inhibitory activity against the iron-induced lipid peroxidation with higher than 90% of inhibitory rates.

With excellent inhibitory activity against lipid peroxidation, the compounds of the present invention can be used as preventive or curative agents for the medical treatment of neurological disorders such as cerebral stroke and dementia, which may be caused by the lipid peroxidation and its accumulation in neurons, as well as for the medical treatment of inflammatory diseases such as arthritis, cardiac infarction, and acute/chronic tissue damage.

Experimental Example 6

Acute Oral Toxicity Test in Rats

The test to confirm the toxicity of the compounds of formula 1 was carried out as follows.

In this test six-week old SPF SD rats were used with two rats assigned to each group. The compounds of examples 2, 6, 10, 11, 19, 20, 25, 26, 30, 34, 35, 36, 39, 40, and 41 were suspended in 0.5% methyl cellulose, respectively, and administered orally at a single dose of 1 g/kg using a ball-tipped needle. The dosing volume was 10 ml/kg. After the administration, the animals were observed for clinical signs of toxicity or mortality and the body weight changes were measured. All survivors at the end of the observation period underwent laparotomy under ether anesthesia and the blood samples were taken from the abdominal aorta for hematological tests and biochemical analysis. After sacrificing the animals, autopsy was performed for macroscopic observation of the organs and tissues. Tissue samples of vital organs from macroscopic legion were removed and fixed in 10% neutral buffered formalin solution, then processed by standard procedures for histopathology and examined under light microscope. There were no significant changes in clinical symptoms, body weight and mortality. Also in hematology, serum chemistry parameters and macroscopic observation, no drug-related changes were observed. As a result all the compounds tested did not show toxicity in rats up to a dose of 1 g/kg, and the lethal dose ($LD_{50}$) for oral administration was determined to be over 1 g/kg in rats.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A compound of formula 1, its isomer or pharmaceutically acceptable salt:

FORMULA 1

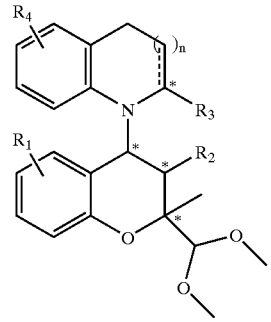

Wherein n is 0 or 1;

$R_1$ represents H, $NO_2$, or $NH_2$;

$R_2$ represents OH, or $O(C=O)R^a$; and $R^a$ represents H; straight or branched alkyl group of $C_1$–$C_4$; or aryl group;

$R_3$ represents H, $C(=O)OR^a$, $CH_2OR^a$, or $C(=O)NR^a{}_2$; and $R^a$ is defined as above;

or $R_2$ and $R_3$ are connected to form lactone ring

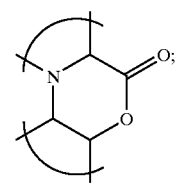

$R_4$ represents H, halogen, OH, or $OR^a$; and $R^a$ is defined as above;

* represents the chiral center;

and single or double bond exists at 2,3-position of heterocycle.

2. The compound of formula 1, its isomer or pharmaceutically acceptable salt according to claim 1, wherein $R_1$ represents $NO_2$ or $NH_2$;

$R_2$ represents OH;

$R_3$ represents $C(=O)OR^a$, or $C(=O)NR^a{}_2$; and $R^a$ represents H; or straight or branched alkyl group of $C_1$–$C_4$;

or $R_2$ and $R_3$ are connected to form lactone ring

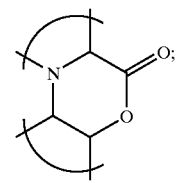

$R_4$ represents H, halogen, OH, or $OCH_3$.

3. The compound of formula 1, its isomer or pharmaceutically acceptable salt according to claim 1, which is a member selected from the group consisting of:
1) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
2) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
3) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
4) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
5) 1-[(2S, 3R, 4S)-3,4-dihydro-2-dimethoxymethyl-3-hydroxy-2-methyl-6-nitro-2H-1-benzopyran-4-yl]-1H-(2R)-2,3-dihydroindole-2-carboxylic acid methyl ester;
6) 1-[(2S, 3R, 4S)-3,4-dihydro-2-dimethoxymethyl-3-hydroxy-2-methyl-6-nitro-2H-1-benzopyran-4-yl]-1H-(2S)-2,3-dihydroindole-2-carboxylic acid methyl ester;
7) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid methyl ester;
8) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid methyl ester;
9) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid;
10) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid isopropyl ester;
11) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
12) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
13) 1-[(2S, 3S, 4R)-3,4-dihydro-2-dimethixymethyl-3-hydroxy-2-methyl-6-nitro-2H-1-benzopyran-4-yl]-(2R)-2,3-dihydro-1H-5-methoxyindole-2-carboxylic acid ethyl ester;
14) 1-[(2S, 3S, 4R)-3,4-dihydro-2-dimethoxymethyl-3-hydroxy-2-methyl-6-nitro-2H-1-bezopyran-4-yl]-(2S)-2,3-dihydro-1H-5-methoxyindole-2-carboxylic acid ethyl ester;
15) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-fluoroindole-2-carboxylic acid;
16) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-fluoroindole-2-carboxylic acid ethyl ester;
17) 1-[(2S, 3S, 4R)-3,4-dihydro-2-dimethoxymetyl-3-hydroxy-2-methyl-6-nitro-2H-1-benzopyran-4-yl]-(2R)-2,3-dihydro-1H-5-fluoroindole-2-carboxylic acid ethyl ester;
18) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-5-fluoroindole-2-carboxylic acid ethyl ester;
19) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester;
20) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
21) 1-[(2S, 3S, 4R)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester;
22) 1-[(2S, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
23) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid methyl ester;
24) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid methyl ester;
25) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl amide;
26) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl amide;
27) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-5-chloro-1H-2-hydroxymethylindole;
28) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-5-chloro-1H-2-hydroxymethylindole;
29) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
30) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
31) 1-[(2R, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
32) 1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
33) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-indole-2-carboxylic acid n-propyl ester;
34) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid n-propyl ester;
35) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
36) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
37) 1-[(2R, 3R, 4S)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
38) 1-[(2R, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;

39) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl amide;
40) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
41) 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester;
42) 1-[(2S, 3R, 4S)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester;
43) 1-[(2S, 3R, 4S)-6-amino-3,4-dihydro-2-dimethoxymethyl-3-hydroxy-2-methyl-2H-1-benzopyran-4-yl]-(2S)-2,3-dihydro-1H-indole-2-carboxylic acid ethyl ester;
44) 1-[(2S, 3S, 4R)-6-amino-3,4-dihydro-2-dimethoxymethyl-3-hydroxy-2-methyl-2H-1-benzopyran-4-yl]-(2R)-2,3-dihydro-1H-indole-2-carboxylic acid ethyl ester;
45) 1-[(2S, 3S, 4R)-6-amino-3,4-dihydro-2-dimethoxymethyl-3-hydroxy-2-methyl-2H-1-benzopyran-4-yl]-(2S)-2,3-dihydro-1H-indole-2-carboxylic acid ethyl ester;
46) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid ethyl ester;
47) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid ethyl ester;
48) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid methyl ester;
49) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid methyl ester;
50) 1-[(2S, 3R, 4S)-3,4-dihydro-2-dimethoxymethyl-3-hydroxy-2-methyl-6-nitro-2H-1-benzopyran-4-yl]-1H-indole-2-carboxylic acid;
51) 1-[(2S, 3S, 4R)-3,4-dihydro-2-dimethoxymethyl-3-hydroxy-2-methyl-6-nitro-2H-1-benzopyran-4-yl]-1H-indole-2-carboxylic acid;
52) 1-[(2S, 3R, 4S)-6-amino-3,4-dihydro-2-dimethoxymethyl-3-hydroxy-2-methyl-2H-1-benzopyran-4-yl]-1H-indole-2-carboxylic acid ethyl ester;
53) 1-[(2S, 3S, 4R)-6-amino-3,4-dihydro-2-dimethoxymethyl-3-hydroxy-2-methyl-2H-1-benzopyran-4-yl]-1H-indole-2-carboxylic acid ethyl ester;
54) 1-[(2S, 3R, 4S)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester;
55) 1-[(2S, 3R, 4S)-3,4-dihydro-2-dimethoxymethyl-3-hydroxy-2-methyl-6-nitro-2H-1-benzopyran-4-yl]-(2S)-1,2,3,4-tetrahydro-1H-quinoline-2-carboxylic acid methyl ester;
56) 1-[(2S, 3S, 4R)-3,4-dihydro-2-dimethoxymethyl-3-hydroxy-2-methyl-6-nitro-2H-1-benzopyran-4-yl]-(2R)-1,2,3,4-tetrahydro-1H-quinoline-2-carboxylic acid methyl ester;
57) 1-[(2S, 3S, 4R)-3,4-dihydro-2-dimethoxymethyl-3-hydroxy-2-methyl-6-nitro-2H-1-benzopyran-4-yl]-(2S)-1,2,3,4-tetrahydro-1H-quinoline-2-carboxylic acid methyl ester;
58) (2S, 2aR, 4aR, 10aS)-[(3,4-b)-2a,10a-dihydro-2-dimethoxymehyl-2-methyl-12-nitro-2H-1-benzopyrano]-[(1,2-d)-4a,5-dihydro-10H-indolino]-4-oxomorpholine;
59) (2S, 2aR, 4aS, 10aS)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;
60) (2S, 2aS, 4aR, 10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;
61) (2S, 2aS, 4aS, 10aR)-[(3,4-b)-2a,10a-dihydro-2-dimethoxymethyl-2-methyl-12-nitro-2H-1-benzopyrano]-[(1,2-d)-4a,5-dihydro-10H-indolino]-4-oxomorpholine;
62) (2S, 2aR, 10aS)-[(3,4-b)-2a,10a-dihydro-2-dimethoxymethyl-2-methyl-12-nitro-2H-1-benzopyrano]-[(1,2-d)-10H-indolino]-4-oxomorpholine; or
63) (2S, 2aS, 10aR)-[(3,4-b)-2a,10a-dihydro-2-dimethoxymethyl-2-methyl-12-nitro-2H-1-benzopyrano]-[(1,2-d)-10H-indolino]-4-oxomorpholine.

4. The compound of formula 1, its isomer or pharmaceutically acceptable salt according to claim 1, which is a member selected from the group consisting of:
1) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
2) 1-[(2S, 3R, 4S)-3,4-dihydro-2-dimethoxymethyl-3-hydroxy-2-methyl-6-nitro-2H-1-benzopyran-4-yl]-1H-(2S)-2,3-dihydroindole-2-carboxylic acid methyl ester;
3) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid isopropyl ester;
4) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
5) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl ester;
6) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
7) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-chloroindole-2-carboxylic acid ethyl amide;
8) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl amide;
9) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
10) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid n-propyl ester;
11) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
12) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;

13) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl amide;
14) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester; or
15) 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester.

5. The compound of formula 1, its isomer or pharmaceutically acceptable salt according to claim 1, which is a member selected from the group consisting of:
1) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-indole-2-carboxylic acid ethyl ester;
2) 1-[(2S, 3R, 4S)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
3) 1-[(2S, 3R, 4S)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester;
4) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-indole-2-carboxylic acid ethyl ester;
5) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-methoxyindole-2-carboxylic acid ethyl ester;
6) 1-[(2R, 3S, 4R)-3,4-dihydro-2-dimethoxymethyl-3-hydroxy-2-methyl-6-nitro-2H-1-benzopyran-4-yl]-(2R)-2,3-dihydro-1H-5-methoxyindole-2-carboxylic acid ethyl ester;
7) 1-[(2R, 3S, 4R)-3,4-dihydro-2-dimethoxymethyl-3-hydroxy-2-methyl-6-nitro-2H-1-benzopyran-4-yl]-(2S)-2,3-dihydro-1H-5-chloroindole-2-carboxylic acid ethyl ester; or
8) 1-[(2R, 3S, 4R)-3,4-dihydro-2-dimethoxymethyl-3-hydroxy-2-methyl-6-nitro-2H-1-benzopyran-4-yl]-1H-(2R)-2,3-dihydro-5-chloroindole-2-carboxylic acid ethyl ester.

6. A process for preparing the compound of claim 1, comprising the step of coupling an epoxide of formula II with a heterocyclic amine of formula III in the presence of a proper coupling agent to obtain a compound of formula I'

Scheme 1

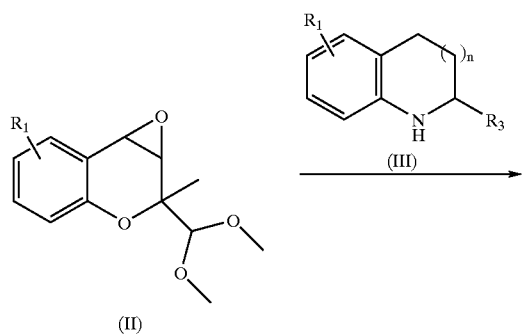

(II)

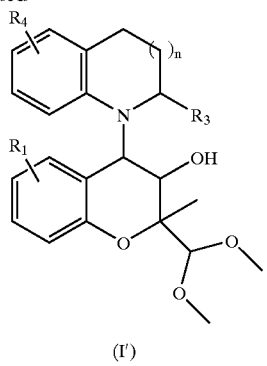

(I')

wherein, $R_1$, $R_3$, $R_4$ and n are defined in claim 1.

7. The process according to claim 6, wherein the coupling agent is selected from the group consisting of $Mg(ClO_4)_2$, $CoCl_2$, NaH, $K_2CO_3$, and t-BuOK.

8. A process for preparing the compound of claim 1 by oxidative aromatization of a benzopyranyl indoline derivative of formula $I_a$.

Scheme 8

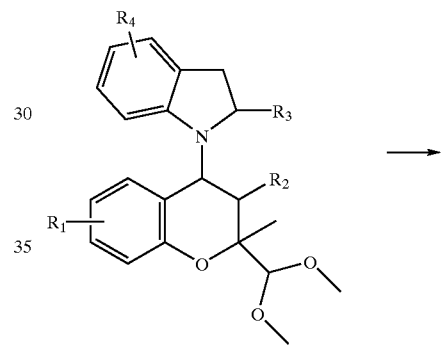

(I$_a$)

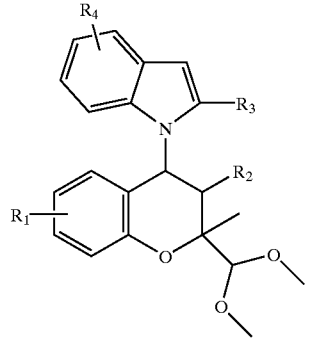

(I$_b$)

wherein, $R_1$, $R_2$, $R_3$ and $R_4$ are defined in claim 1.

9. The process according to claim 8, wherein the oxidative aromatization is performed in the presence of an oxidizing agent selected from the group consisting of $MnO_2$ and DDQ.

10. A pharmaceutical composition comprising as an active ingredient an effective amount of the compound of claim 1, or its pharmaceutically acceptable salt.

11. A method of treatment or prevention of cardiovascular disease, said method comprising administering to a patient in need thereof an effective amount of the pharmaceutical composition of claim 10.

12. A method according to claim 11, wherein the cardiovascular disease is myocardial infraction or congestive heart failure.

13. A method of treatment or prevention of a neurodegenerative disorder caused by damage or death of neuronal cells, said method comprising administering to a patient in need thereof an effective amount of the pharmaceutical composition of claim 10.

14. A method according to claim 13, wherein the neurodegenerative disorder is selected from the group consisting of stroke, infant asphyxia, glaucoma and diabetic neuropathy.

15. A method of suppressing of lipid preoxidation, said method comprising administering to a patient in need thereof an effective amount of the pharmaceutical composition of claim 10.

16. A method of preserving an organ, said method comprising administering to a patient in need thereof an effective amount of the pharmaceutical composition of claim 10.

17. A method according to claim 16, wherein the organ is selected from the group consisting of heart, kidney, liver and tissue.

* * * * *